(12) United States Patent
Elbeck

(10) Patent No.: US 10,515,723 B2
(45) Date of Patent: Dec. 24, 2019

(54) ELECTRONIC GROUP MANAGEMENT SYSTEM

(71) Applicant: ONCALLPEOPLE, Cary, NC (US)

(72) Inventor: Osama Elbeck, Cary, NC (US)

(73) Assignee: ONCALLPEOPLE, Cary, NC (US)

( * ) Notice: Subject to any disclaimer, the term of this patent is extended or adjusted under 35 U.S.C. 154(b) by 0 days.

(21) Appl. No.: 15/869,881

(22) Filed: Jan. 12, 2018

(65) Prior Publication Data

US 2019/0221305 A1 Jul. 18, 2019

(51) Int. Cl.
*G16H 40/20* (2018.01)
*H04W 4/08* (2009.01)
*H04M 3/51* (2006.01)
*H04M 3/523* (2006.01)

(52) U.S. Cl.
CPC .......... *G16H 40/20* (2018.01); *H04M 3/5116* (2013.01); *H04M 3/523* (2013.01); *H04W 4/08* (2013.01); *H04M 2207/18* (2013.01)

(58) Field of Classification Search
CPC .... G16H 40/20; H04M 3/5116; H04M 3/523; H04M 2207/18; H04W 4/08
USPC ............ 379/211.02, 212.01, 214.01, 265.04, 379/265.05
See application file for complete search history.

(56) References Cited

U.S. PATENT DOCUMENTS

| | | | |
|---|---|---|---|
| 6,647,107 B1 * | 11/2003 | Horrer | H04M 3/51 379/214.01 |
| 7,691,059 B2 | 4/2010 | Bulat | |
| 8,468,030 B2 | 6/2013 | Stroup et al. | |
| 9,269,116 B2 | 2/2016 | Bulat | |
| 9,430,805 B2 | 8/2016 | Bulat | |
| 2002/0131572 A1 * | 9/2002 | Paradis | G16H 40/20 379/200 |
| 2008/0101565 A1 | 5/2008 | Tyler | |
| 2015/0332001 A1 | 11/2015 | Goldfein et al. | |
| 2015/0370974 A1 | 12/2015 | Zebarjadi et al. | |

(Continued)

FOREIGN PATENT DOCUMENTS

| CN | 102314558 A | 1/2012 |
|---|---|---|
| CN | 102664940 A | 9/2012 |

(Continued)

*Primary Examiner* — Harry S Hong
(74) *Attorney, Agent, or Firm* — Burr & Forman LLP

(57) ABSTRACT

A method for providing electronic group management that integrates scheduling, personnel management and communication functions may include associating a provider group with an exchange number such that the exchange number is immediately accessible to receive phone calls for on call services associated with the provider group. The method may further include associating a plurality of service providers with the provider group and associating at least one of the service providers with one or more temporal segments of a dynamically updateable reference schedule to define the at least one of the service providers as an on call service provider for the one or more temporal segments of the dynamically updateable reference schedule. The method may also include, in response to receiving a call to the exchange number, forwarding the call to the on call service provider associated with a given temporal segment via contact information associated with the on call service provider via the dynamically updateable reference schedule.

20 Claims, 18 Drawing Sheets

(56) References Cited

U.S. PATENT DOCUMENTS

| | | | |
|---|---|---|---|
| 2016/0080574 A1* | 3/2016 | Huynh | H04M 3/5191 379/202.01 |
| 2016/0125168 A1 | 5/2016 | Aagesen et al. | |

FOREIGN PATENT DOCUMENTS

| | | |
|---|---|---|
| CN | 103455960 A | 12/2013 |
| CN | 104657927 A | 5/2015 |
| CN | 104732468 A | 6/2015 |
| CN | 104820903 A | 8/2015 |
| CN | 105373871 A | 3/2016 |
| CN | 105380765 A | 3/2016 |
| CN | 105468892 A | 4/2016 |
| CN | 104134267 B | 9/2016 |
| CN | 105979110 A | 9/2016 |
| CN | 106169022 A | 11/2016 |
| CN | 103632324 B | 1/2017 |
| CN | 106485355 A | 3/2017 |
| CN | 106650258 A | 5/2017 |
| CN | 106845126 A | 6/2017 |
| CN | 106934244 A | 7/2017 |
| CN | 106951712 A | 7/2017 |
| CN | 107169293 A | 9/2017 |
| CN | 107220516 A | 9/2017 |
| CN | 107332964 A | 11/2017 |
| IN | 3783/DEL/2014 | 11/2015 |
| JP | 2004318751 A | 11/2004 |
| JP | 2010015255 A | 1/2010 |
| JP | 2010033388 A | 2/2010 |
| JP | 2011044041 A | 3/2011 |
| KR | 101164196 B1 | 7/2012 |
| KR | 20170054354 A | 5/2017 |
| WO | 2016201745 A1 | 12/2016 |

* cited by examiner

FIG. 6.

ELECTRONIC GROUP MANAGEMENT SYSTEM

TECHNICAL FIELD

Example embodiments generally relate to group management systems and, in particular, relate to an electronic asset management tool that can integrate a number of technical modules to effectively and efficiently provide group management in complex environments such as a healthcare environment.

BACKGROUND

The healthcare industry continues to see technology leveraged to provide improved outcomes for patients as new drugs and equipment give physicians ever improving tools to assess and treat disease. Meanwhile, technology has also been used by the healthcare industry to attempt to manage the many people, places and pieces of equipment that form the backbone of the various healthcare systems and hospitals that exist throughout the country. The goals of improving the quality of patient care while attempting to also control cost provide a seemingly endless supply of incentive to technology companies to develop tools for use by the healthcare industry. However, these tools, as effective as they may sometimes be, have often tended to be very focused on a specific pain point for healthcare systems resulting in a number of silos or islands of innovation that do not work with or reinforce each other. As a result, each healthcare system ends up managing a fragmented system of electronic tools that each aim to be helpful with respect to a limited scope of problems.

Accordingly, in the 24×7 world of patient care and personnel management, there remains a need to provide an integrated group management solution that is both cost effective and efficient.

BRIEF DESCRIPTION OF THE SEVERAL VIEWS OF THE DRAWING(S)

Having thus described the invention in general terms, reference will now be made to the accompanying drawings, which are not necessarily drawn to scale, and wherein:

FIG. 6 illustrates an example patient management page according to an example embodiment;

FIG. 17, which includes

BRIEF SUMMARY OF SOME EXAMPLES

Figure 1:
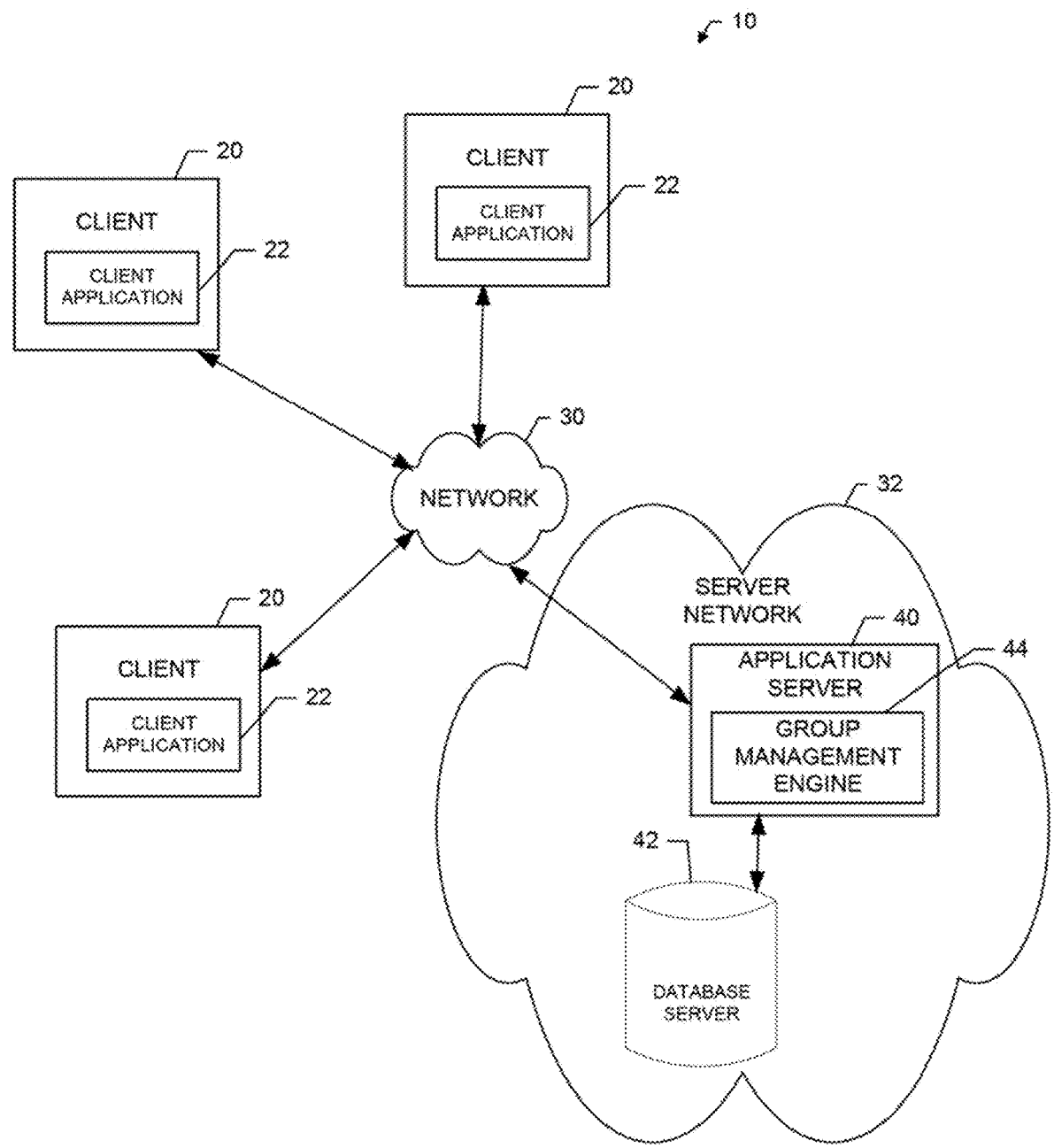
FIG. 1 illustrates a functional block diagram of a system that may be useful in connection with providing electronic group management according to an example embodiment.

In accordance with an example embodiment, a system for providing electronic group management that integrates scheduling, personnel management and communication functions is provided. The system may include processing circuitry configured to associate a provider group with an exchange number such that the exchange number is immediately accessible to receive phone calls for on call services associated with the provider group, associate a plurality of service providers with the provider group, and associate at least one of the service providers with one or more temporal segments of a dynamically updateable reference schedule to define the at least one of the service providers as an on call service provider for the one or more temporal segments of the dynamically updateable reference schedule. Within this context, the dynamically updateable reference schedule may provide corresponding voice call contact information and data messaging contact information for each of the service providers of the provider group such that calls to the exchange number are forwarded to the on call service provider associated with a given temporal segment via voice call contact information of the on call provider, and a modification to the dynamically updateable reference schedule at the given temporal segment triggers a notification to be sent to data messaging contact information of each service provider associated with the given temporal segment responsive to a modification to the dynamically updateable reference schedule at the given temporal segment.

In accordance with another example embodiment, a method for providing electronic group management that integrates scheduling, personnel management and communication functions is provided. The method may include associating a provider group with an exchange number such that the exchange number is immediately accessible to receive phone calls for on call services associated with the provider group. The method may further include associating a plurality of service providers with the provider group and associating at least one of the service providers with one or more temporal segments of a dynamically updateable reference schedule to define the at least one of the service providers as an on call service provider for the one or more temporal segments of the dynamically updateable reference schedule. The method may also include, in response to receiving a call to the exchange number, forwarding the call to the on call service provider associated with a given temporal segment via contact information associated with the on call service provider via the dynamically updateable reference schedule.

In accordance with still another example embodiment, a method for providing electronic group management that integrates scheduling, personnel management and communication functions that enables automatic notification of certain activities is provided. The method may include associating a plurality of service providers with a provider group and associating at least one of the service providers with one or more temporal segments of a dynamically updateable reference schedule to define the at least one of the service providers as an on call service provider for the one or more temporal segments of the dynamically updateable reference schedule. The method may further include, in response to receiving a modification to the dynamically updateable reference schedule at a given temporal segment to which a given on call service provider is associated, triggering a notification to be sent to the given on call service provider associated with the given temporal segment.

DETAILED DESCRIPTION

Some example embodiments now will be described more fully hereinafter with reference to the accompanying drawings, in which some, but not all example embodiments are shown. Indeed, the examples described and pictured herein should not be construed as being limiting as to the scope, applicability or configuration of the present disclosure. Rather, these example embodiments are provided so that this disclosure will satisfy applicable legal requirements. Like reference numerals may be used to refer to like elements throughout. Furthermore, as used herein, the term "or" is to be interpreted as a logical operator that results in true whenever one or more of its operands are true.

As used in herein, the terms "component," "module," and the like are intended to include a computer-related entity, such as but not limited to hardware, firmware, or a combination of hardware and software (i.e., hardware being configured in a particular way by software being executed thereon). For example, a component or module may be, but is not limited to being, a process running on a processor, a processor (or processors), an object, an executable, a thread of execution, and/or a computer. By way of example, both an application running on a computing device and/or the computing device can be a component or module. One or more components or modules can reside within a process and/or thread of execution and a component/module may be localized on one computer and/or distributed between two or more computers. In addition, these components can execute from various computer readable media having various data structures stored thereon. The components may communicate by way of local and/or remote processes such as in accordance with a signal having one or more data packets, such as data from one component/module interacting with another component/module in a local system, distributed system, and/or across a network such as the Internet with other systems by way of the signal. Each respective component/module may perform one or more functions that will be described in greater detail herein. However, it should be appreciated that although this example is described in terms of separate modules corresponding to various functions performed, some examples may not necessarily utilize modular architectures for employment of the respective different functions. Thus, for example, code may be shared between different modules, or the processing circuitry itself may be configured to perform all of the functions described as being associated with the components/modules described herein. Furthermore, in the context of this disclosure, the term "module" should not be understood as a nonce word to identify any generic means for performing functionalities of the respective modules. Instead, the term "module" should be understood to be a modular component that is specifically configured in, or can be operably coupled to, the processing circuitry to modify the behavior and/or capability of the processing circuitry based on the hardware and/or software that is added to or otherwise operably coupled to the processing circuitry to configure the processing circuitry accordingly.

As discussed above, healthcare systems currently manage a number of different or fragmented management solutions that are each related to different aspects of patient care and personnel management. For example, different electronic systems may be used to manage scheduling and connectivity for on-call services. Different electronic systems may also be used to manage vacation and sick time, patient rounding and patient handoff, all within a context that must remain compliant with the requirements of HIPAA (Health Insurance Portability and Accountability Act). Some example embodiment may provide a modular group management system that may be particularly effective in environments such as those that exist in the healthcare industry. In this regard, for example, some embodiments may provide smart scheduling services that are fully integrated in a real time environment with physician management and telephone exchange services. Accordingly, for example, enterprise level management of a number of inter-related services can be provided by a single platform. Moreover, since the platform is modular in nature, additional modules can easily be added to expand the capabilities of the system and also expand the levels of integration that can be provided by the system.

An example embodiment of the invention will now be described in reference to FIG. 1, which illustrates an example system in which an embodiment of the present invention may be employed. As shown in FIG. 1, a system 10 according to an example embodiment may include one or more client devices (e.g., clients 20). Notably, although FIG. 1 illustrates three clients 20, it should be appreciated that a single client or many more clients 20 may be included in some embodiments and thus, the three clients 20 of FIG. 1 are simply used to illustrate a potential for a multiplicity of clients 20 and the number of clients 20 is in no way limiting to other example embodiments. In this regard, example embodiments are scalable to inclusion of any number of clients 20 being tied into the system 10.

The clients 20 may, in some cases, each be associated with a single organization, department within an organization, or location (i.e., with each one of the clients 20 being associated with an individual department of an organization, team or location). However, in some embodiments, each of the clients 20 may be associated with different corresponding locations, departments or organizations. For example, among the clients 20, one client may be associated with a first facility of a first organization and one or more of the other clients may be associated with a second facility of either the first organization or of another organization. In some cases, one or more of the clients 20 may also be associated with individuals associated with an organization, department, location, etc. Thus, for example, one or more of the clients 20 may be a smart phone, tablet or computer associated with an individual (e.g., a physician or other service provider) and one or more other ones of the clients 20 may be associated with a supervisor or supervisory function and/or other participants or users of information within the system 10 (e.g., a nurses station, individual nurses, patients, etc.).

Each one of the clients 20 may include or otherwise be embodied as computing device (e.g., a computer, a network access terminal, a personal digital assistant (PDA), cellular phone, smart phone, tablet, or the like) capable of communication with a network 30. As such, for example, each one of the clients 20 may include (or otherwise have access to) memory for storing instructions or applications for the performance of various functions and a corresponding processor for executing stored instructions or applications. Each one of the clients 20 may also include software and/or corresponding hardware for enabling the performance of the respective functions of the clients 20 as described below. In an example embodiment, one or more of the clients 20 may include a client application 22 configured to operate in accordance with an example embodiment of the present invention. In this regard, for example, the client application 22 may include software for enabling a respective one of the clients 20 to communicate with the network 30 for requesting and/or receiving information and/or services via the network 30. Moreover, in some embodiments, the information or services that are requested via the network may be provided in a software as a service (SaaS) environment. The information or services receivable at the client applications 22 may include deliverable components (e.g., downloadable software to configure the clients 20, or information for consumption/processing at the clients 20). As such, for example, the client application 22 may include corresponding executable instructions for configuring the client 20 to provide corresponding functionalities for processing and/or communication of information/requests as described in greater detail below.

The network 30 may be a data network, such as a local area network (LAN), a metropolitan area network (MAN), a wide area network (WAN) (e.g., the Internet), and/or the like, which may couple the clients 20 to devices such as processing elements (e.g., personal computers, server computers or the like) and/or databases. Communication between the network 30, the clients 20 and the devices or databases (e.g., servers) to which the clients 20 are coupled may be accomplished by either wireline or wireless communication mechanisms and corresponding communication protocols.

In an example embodiment, devices to which the clients 20 may be coupled via the network 30 may include one or more application servers (e.g., application server 40), and/or a database server 42, which together may form respective elements of a server network 32. Although the application server 40 and the database server 42 are each referred to as "servers," this does not necessarily imply that they are embodied on separate servers or devices. As such, for example, a single server or device may include both entities and the database server 42 could merely be represented by a database or group of databases physically located on the same server or device as the application server 40. The application server 40 and the database server 42 may each include hardware and/or software for configuring the application server 40 and the database server 42, respectively, to perform various functions. As such, for example, the application server 40 may include processing logic and memory enabling the application server 40 to access and/or execute stored computer readable instructions for performing various functions. In an example embodiment, one function that may be provided by the application server 40 may be the provision of access to information and/or services related to operation of the terminals or computers with which the clients 20 are associated. For example, the application server 40 may be configured to provide for storage of information and/or instructions for providing schedule management services and/or the responses/actions to be taken when information or requests are received. In some cases, these contents may be stored in the database server 42. Alternatively or additionally, the application server 40 may be configured to provide communication and scheduling tools for use by the clients 20 in accordance with example embodiments.

In some embodiments, for example, the application server 40 may therefore include an instance of a group management engine 44 comprising stored instructions for handling activities associated with practicing example embodiments as described herein. As such, in some embodiments, the clients 20 may access the group management engine 44 online and utilize the services provided thereby. However, it should be appreciated that in other embodiments, the group management engine 44 may be provided from the application server 40 (e.g., via download over the network 30) to one or more of the clients 20 to enable recipient clients to instantiate an instance of the group management engine 44 for local operation. As yet another example, the group management engine 44 may be instantiated at one or more of the clients 20 responsive to downloading instructions from a removable or transferable memory device carrying instructions for instantiating the group management engine 44 at the corresponding one or more of the clients 20. In such an example, the network 30 may, for example, be a peer-to-peer (P2P) network where one of the clients 20 includes an instance of the group management engine 44 to enable the corresponding one of the clients 20 to act as a server to other clients 20.

In an example embodiment, the application server 40 may include or have access to memory (e.g., internal memory or the database server 42) for storing instructions or applications for the performance of various functions and a corresponding processor for executing stored instructions or applications. For example, the memory may store an instance of the group management engine 44 configured to operate in accordance with an example embodiment of the present invention. In this regard, for example, the group management engine 44 may include software for enabling the application server 40 to communicate with the network 30 and/or the clients 20 for the provision and/or receipt of information associated with performing activities as described herein. Moreover, in some embodiments, the application server 40 may include or otherwise be in communication with an access terminal (e.g., a computer including a user interface) via which analysts may interact with, configure or otherwise maintain the system 10.

As such, the environment of FIG. 1 illustrates an example in which provision of content and information associated with the management of various activities associated with a particular group so that scheduling and communication may be accomplished by a particular entity (namely the group management engine 44 residing at the application server 40). However, it should be noted again that the group management engine 44 could alternatively handle provision of content and information within a single organization or multiple organizations/departments. Thus, in some embodiments, the group management engine 44 may be embodied at one or more of the clients 20 and, in such an example, the group management engine 44 may be configured to handle provision of content and information associated with scheduling/communication tasks that are associated only with the corresponding single organization or with multiple organizations/departments. Access to the group management engine 44 may therefore be secured as appropriate for the organization or department involved and credentials of individuals or managers attempting to utilize the tools provided herein.

Figure 2:
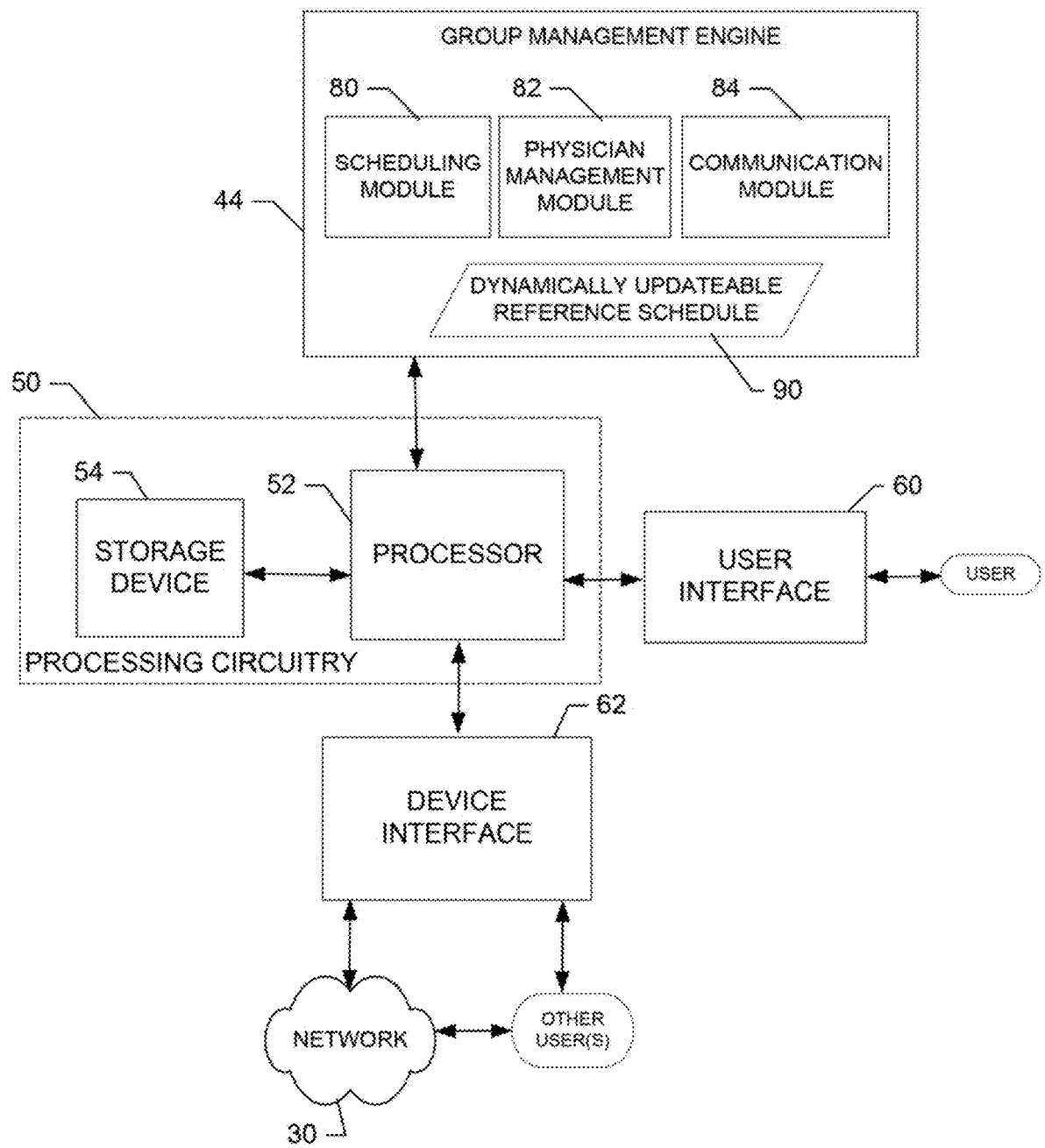
FIG. 2 illustrates a functional block diagram of an apparatus that may be useful in connection with providing electronic group management according to an example embodiment.

An example embodiment of the invention will now be described with reference to FIG. 2. FIG. 2 shows certain elements of an apparatus for provision of integrated scheduling, personnel management and communication services (e.g., telephone exchange, email, text messaging, etc.) according to an example embodiment. The apparatus of FIG. 2 may be employed, for example, on a client (e.g., any of the clients 20 of FIG. 1) or a variety of other devices (such as, for example, a network device, server, proxy, or the like (e.g., the application server 40 of FIG. 1)). Alternatively, embodiments may be employed on a combination of devices. Accordingly, some embodiments of the present invention may be embodied wholly at a single device (e.g., the application server 40 or one or more clients 20) or by devices in a client/server relationship (e.g., the application server 40 and one or more clients 20). Furthermore, it should be noted that the devices or elements described below may not be mandatory and thus some may be omitted in certain embodiments.

Referring now to FIG. 2, an apparatus for electronic group management including provision of integrated scheduling, personnel management and communication services is provided. The apparatus may be an embodiment of the group management engine 44 or a device hosting the group management engine 44. As such, configuration of the apparatus as described herein may transform the apparatus into the group management engine 44. In an example embodiment, the apparatus may include or otherwise be in communication with processing circuitry 50 that is configured to perform data processing, application execution and other processing and management services according to an example embodiment of the present invention. In one embodiment, the processing circuitry 50 may include a storage device 54 and a processor 52 that may be in communication with or otherwise control a user interface 60 and a device interface 62. As such, the processing circuitry 50 may be embodied as a circuit chip (e.g., an integrated circuit chip) configured (e.g., with hardware, software or a combination of hardware and software) to perform operations described herein. However, in some embodiments, the processing circuitry 50 may be embodied as a portion of a server, computer, laptop, workstation or even one of various mobile computing devices. In situations where the processing circuitry 50 is embodied as a server or at a remotely located computing device, the user interface 60 may be disposed at another device (e.g., at a computer terminal or client device such as one of the clients 20) that may be in communication with the processing circuitry 50 via the device interface 62 and/or a network (e.g., network 30).

The user interface 60 may be in communication with the processing circuitry 50 to receive an indication of a user input at the user interface 60 and/or to provide an audible, visual, mechanical or other output to the user. As such, the user interface 60 may include, for example, a keyboard, a mouse, a joystick, a display, a touch screen, a microphone, a speaker, a cell phone, or other input/output mechanisms. In embodiments where the apparatus is embodied at a server or other network entity, the user interface 60 may be limited or even eliminated in some cases. Alternatively, as indicated above, the user interface 60 may be remotely located.

The device interface 62 may include one or more interface mechanisms for enabling communication with other devices and/or networks. In some cases, the device interface 62 may be any means such as a device or circuitry embodied in either hardware, software, or a combination of hardware and software that is configured to receive and/or transmit data from/to a network and/or any other device or module in communication with the processing circuitry 50. In this regard, the device interface 62 may include, for example, an antenna (or multiple antennas) and supporting hardware and/or software for enabling communications with a wireless communication network and/or a communication modem or other hardware/software for supporting communication via cable, digital subscriber line (DSL), universal serial bus (USB), Ethernet or other methods. In situations where the device interface 62 communicates with a network, the network may be any of various examples of wireless or wired communication networks such as, for example, data networks like a Local Area Network (LAN), a Metropolitan Area Network (MAN), and/or a Wide Area Network (WAN), such as the Internet.

In an example embodiment, the storage device 54 may include one or more non-transitory storage or memory devices such as, for example, volatile and/or non-volatile memory that may be either fixed or removable. The storage device 54 may be configured to store information, data, applications, instructions or the like for enabling the apparatus to carry out various functions in accordance with example embodiments of the present invention. For example, the storage device 54 could be configured to buffer input data for processing by the processor 52. Additionally or alternatively, the storage device 54 could be configured to store instructions for execution by the processor 52. As yet another alternative, the storage device 54 may include one of a plurality of databases (e.g., database server 42) that may store a variety of files, contents or data sets. Among the contents of the storage device 54, applications (e.g., client application 22 or service application 42) may be stored for execution by the processor 52 in order to carry out the functionality associated with each respective application.

The processor 52 may be embodied in a number of different ways. For example, the processor 52 may be embodied as various processing means such as a microprocessor or other processing element, a coprocessor, a controller or various other computing or processing devices including integrated circuits such as, for example, an ASIC (application specific integrated circuit), an FPGA (field programmable gate array), a hardware accelerator, or the like. In an example embodiment, the processor 52 may be configured to execute instructions stored in the storage device 54 or otherwise accessible to the processor 52. As such, whether configured by hardware or software methods, or by a combination thereof, the processor 52 may represent an entity (e.g., physically embodied in circuitry) capable of performing operations according to embodiments of the present invention while configured accordingly. Thus, for example, when the processor 52 is embodied as an ASIC, FPGA or the like, the processor 52 may be specifically configured hardware for conducting the operations described herein. Alternatively, as another example, when the processor 52 is embodied as an executor of software instructions, the instructions may specifically configure the processor 52 to perform the operations described herein.

In an example embodiment, the processor 52 (or the processing circuitry 50) may be embodied as, include or otherwise control the group management engine 44, which may be any means such as a device or circuitry operating in accordance with software or otherwise embodied in hardware or a combination of hardware and software (e.g., processor 52 operating under software control, the processor 52 embodied as an ASIC or FPGA specifically configured to perform the operations described herein, or a combination thereof) thereby configuring the device or circuitry to perform the corresponding functions of the group management engine 44 as described below.

The group management engine 44 may include tools to facilitate the aggregation of physician management data or other information associated with personnel management for a group along with smart scheduling and communication services to make all available services accessible via the network 30 remotely and in real-time (or substantially in real-time). The group management engine 44 may also include tools to facilitate the creation, management and distribution of scheduling information for the group via the network 30, and also provide an integrated information distribution platform so that scheduling services and the needed communication of information for managing the schedule are all handled through a single, real time service. In an example embodiment, the group management engine 44 may include a number of components or modules that are each configured to handle various aspects of the overall services that are provided by the group management engine 44. Each of the components or modules may be individually configured to perform one or more of the individual tasks or functions generally attributable to the group management engine 44. For example, the group management engine 44 may include a scheduling module 80, a physician management module 82 and a communication module 84.

In some embodiments, the group management engine 44 and/or any modules comprising the group management engine 44 may be any means such as a device or circuitry operating in accordance with software or otherwise embodied in hardware or a combination of hardware and software (e.g., processor 52 operating under software control, the processor 52 embodied as an ASIC or FPGA specifically configured to perform the operations described herein, or a combination thereof) thereby configuring the device or circuitry to perform the corresponding functions of the group management engine 44 and/or any modules thereof, as described herein. As such, each of the modules (e.g., the scheduling module 80, the physician management module 82 and the communication module 84) may include processing circuitry (e.g., the processing circuitry 50) that is configured to perform the functionality of the corresponding module.

In an example embodiment, the scheduling module 80 may be configured to enable definition of a dynamically updateable reference schedule 90 that can be used to integrate information from various sources to define service provider groups that are updateable and reachable in real time, and to enable information exchange (e.g., notifications/requests/approvals, etc.) in an automated fashion in accordance with example embodiments. In this regard, the dynamically updateable reference schedule 90 may have temporal segments that represent divisions of time in a period to be managed (e.g., day, week, month, year, etc.). The temporal segments may be associated with a group of service providers, and the group may be associated with an exchange number that can be reached as soon as the group is created. The group may be populated with physicians that each have corresponding individual contact information associated therewith (e.g., provider identity information). The scheduling module 80 may also be configured to generate various interfaces for enabling managers, service providers, and those in need of service (e.g., nurses, other physicians, or patients) to interact with the system 10. Thus, managers may define the dynamically updateable reference schedule 90 and service providers may provide input for the definition of the dynamically updateable reference schedule 90 and/or request modifications thereto.

The dynamically updateable reference schedule 90 may be created by the scheduling module 80, but may be accessed by other modules, and other modules may be accessed for creation of the dynamically updateable reference schedule 90. For example, the physician management module 82 may be configured to provide physician information (e.g., the provider identity information) for each service provider that interacts with the group management engine 44. The provider identity information may include voice call contact information (e.g., a personal cell phone number or home telephone number of the physician or service provider) and data messaging contact information (e.g., an email address) to enable both voice calls to be routed to each individual and notification messages to be routed to each individual. The physician management module 82 may also be configured to generate various interfaces for enabling managers and service providers to interact with the system 10 to perform various management functions or request and receive responses to requests related to such functions. For example, physicians can update their provider identity information, and such information will be immediately updated within the system 10 so that any call that is to be routed to a particular service provider who just changed his/her contact information (e.g., due to getting a new phone or being at a designated location) can immediately be reached at the updated contact information.

In an example embodiment, the communication module 84 may be configured to coordinate and/or control all messaging and contact functions of the group management engine 44. Thus, for example, the communication module 84 may be configured to generate emails, text messages, initiate calls to individual service providers responsive to calls made to the group to which a service provider is associated and/or the like. The communication module 84 may also be configured to activate a new exchange number (e.g., a telephone number, voice over IP (VOIP) call number, 1-800 number, etc.) for each group that is created immediately upon group creation. Thus, for example, if a new group is created, the new group will have the new exchange number generated and activated so that any call made to the new exchange number will be answered by the communication module 84 and processed according to protocols defined by the communication module 84. In some cases, the communication module 84 may define an automated interface enabling voice or key commands to be used to navigate the automated interface. In an example embodiment, the automated interface may guide callers through options including, for example, reaching the on call service provider. If the caller selects an option for reaching the on call service provider, the communication module 84 may reference the dynamically updateable reference schedule 90 to determine the specific service provider currently on call. The communication module 84 may then immediately use the provider identity information for the specific service provider currently on call to connect the caller to the specific service provider currently on call. Other options may also be available such as, for example, enabling the physician to interact with the dynamically updateable reference schedule 90 using voice or key commands to update information or request changes to the dynamically updateable reference schedule 90. The communication module 84 may be interconnected with the scheduling module 80 and the physician management module 82 to process these updates in real time so that any changes that are requested and either authorized or approved can be immediately updated. Any parties impacted by updates may then be notified (e.g., via email or text message) to ensure that all impacted parties are informed.

As such, for example, the communication module 84 may manage all communications to and from the group management engine 44 and/or any modules thereof. In particular, the communication module 84 ensures that groups are created and contactable in real time, and that any changes made to schedules associated with the groups are communicated to all individuals who should be informed of such changes. The changes may be specific requests, or routine events that happen due to the passage of time (e.g., shift change due to one temporal segment ending and another beginning). Changes responsive to either are implemented by the system immediately. Thus, if a service provider requests and is granted a change, the change is reflected and implemented immediately upon approval. If the time for a shift change passes, the communication module 84 will route incoming calls for service to the new on call service provider immediately after the time passes to trigger a shift change.

The communication module 84 therefore has an on call processing function (i.e., real time processing of calls for service to ensure they are routed to the proper service provider), and a notification function (i.e., processing and notification of requests for changes to the dynamically updateable reference schedule 90 and for communicating changes made to the dynamically updateable reference schedule 90 to those impacted). Thus, the communication module 84 provides the communication interface to the dynamically updateable reference schedule 90, which effectively creates a schedule-integrated telephone exchange system that further includes the capability to modify and generate immediate notifications of modifications to the schedule.

In some cases, other functions besides on call service related functions may also be managed by the modules of the group management engine 44. For example, in an example embodiment, the group management engine 44 may provide services related to managing rounding schedules in a health care context. In this context, a schedule (e.g., similar to the dynamically updateable reference schedule 90 described above) may be defined for rounding physicians. The group management engine 44 may include a module or modules (either in addition to those described above, or those described above may also be configured accordingly) to manage patient distribution for the rounding physicians. Within such context, the schedule may initially be consulted to determine which physicians are scheduled for rounding. An initial patient count may then be determined for each physician. The physicians may then be ranked in order (e.g., in ascending order) based on patient count. Patients may then be distributed to physicians from top to bottom relative to this ranking in one of two ways. First, a doctor a with lower patient count may be assigned patients until the number of patients for the doctor equals the next lowest doctor. Thereafter, patients are distributed to the doctor and the next lowest doctor alternately until the number of patients assigned to each of these doctors reaches the doctor with the third lowest count. This process may then be continued until all patients have been assigned.

In a second distribution paradigm, patients can be distributed regardless of their census. For example, patient categories may be defined and used as an input relative to patient distribution so that patients can be distributed at least in part based on patient status, time by which patients are to be seen, etc. Thus, patients identified as "patients to be seen before midnight with a status of OBSERVATION," patients identified as "patients to be seen after midnight with a status of OBSERVATION," or patients identified as "UNSEEN PATIENTS" can be distributed amongst physicians based on timing and status considerations. In some cases, patients may be scored, ranked or weighted based on a level of difficulty of the treatment associated with each patient. Thus, for example, patient distribution can not only be performed based on numbers of patients, but based on achieving equality in a weighted average of patient care tasking since each task can be assigned a corresponding weight.

In some cases, one or more of the physicians may be capped in terms of the number of patients that can be assigned thereto. When a physician reaches a capped value, no additional patients will be assigned regardless of the status of the assignment method described above. However, if all physicians reach their respective capped values, then further assignment may continue alternately to each respective physician. Thus, in some cases, the group management engine 44 may be configured to distribute patients based on a ratio (weighted or otherwise) of physicians to patients to ensure that no one physician is overburdened with a heavy load of patients while other physicians have lighter loads.

Operation of the modules above in accordance with an example embodiment will now be described in general terms in relation to FIGS. 3-14, which shows various screen shots that could be generated at the user interface 60 responsive to operation of an example embodiment. As can be appreciated from FIG. 3, a user may login to access the group management engine 44 from any one of the clients 20 of FIG. 1. The interface generated, security access and functional enablement provided for the user may depend on credentials used by the user to login. For example, if the user is a manager, different types of interfaces related to managing requests and defining schedules may be provided. However, if the user is a physician, the interfaces may be limited to changing contact information, making schedule change requests, and referencing information on a schedule that is for a group to which the physician is assigned may be provided. If the user is a nurse or other user of services, still other interfaces may be generated. The interfaces generated may be controlled, in some cases, by the communication module 84.

The user may initially be provided with a dashboard display 100, which may display a number of information boxes 110. The information boxes 110 may each be provided with different specific pieces of information that may be applicable to the user. In some cases, the user may be enabled to customize the location, size and/or types of information that are shown on the dashboard display 100. In an example embodiment, each user (by type or classification of user (e.g., physician, nurse, patient, manager, etc.)) may have a standard or default group of information boxes 110, and the user may (if desired) change the information boxes 110 based on settings selected by the user.

Figure 3:
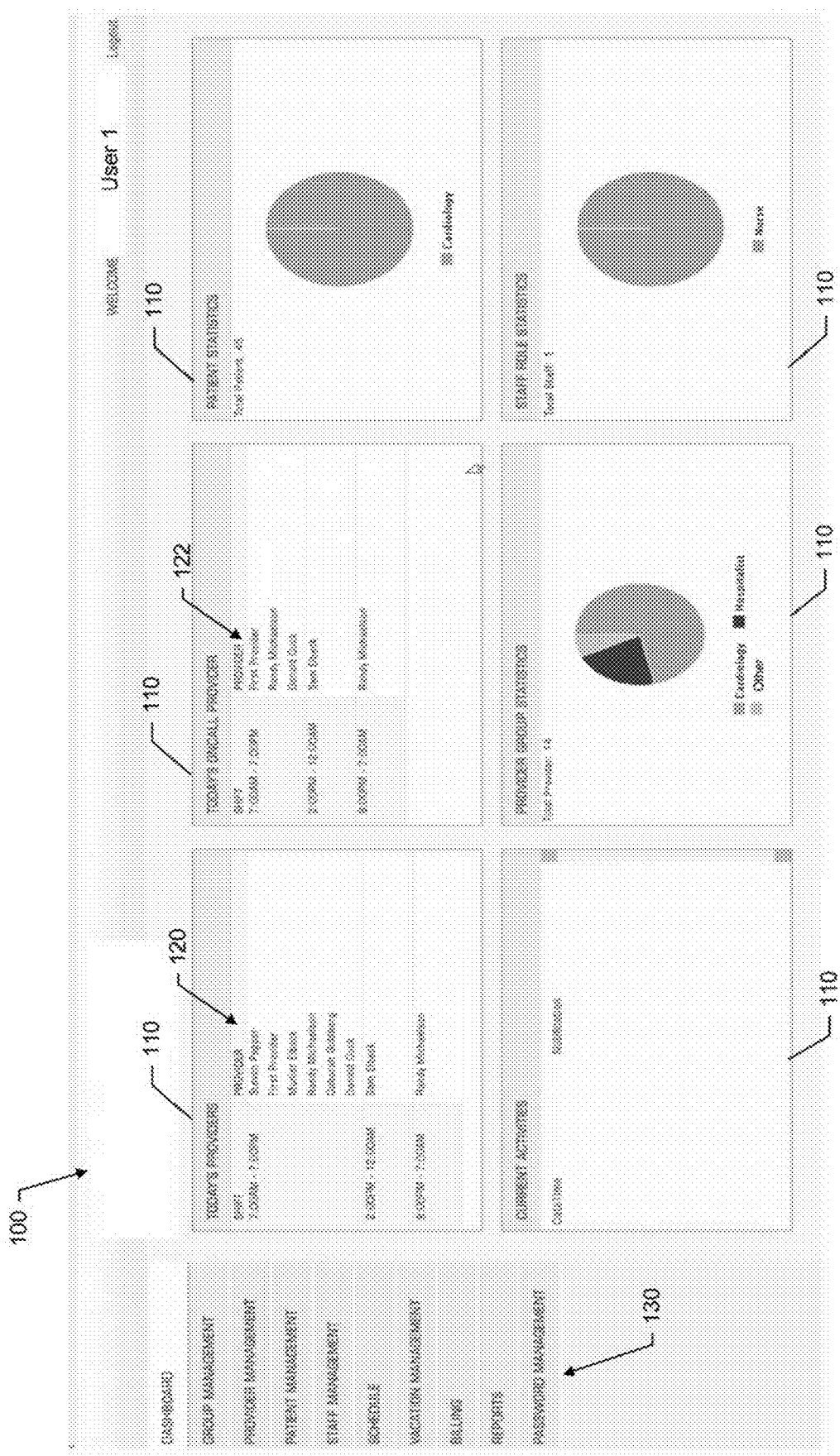
FIG. 3 illustrates an example dashboard display in accordance with an example embodiment.

In the example of FIG. 3, a listing 120 of service providers (e.g., physicians) on shift may be provided along with the corresponding time slots for each of the providers in one of the information boxes 110. A listing 122 of on-call providers and corresponding times may also be provided in another information box 110. Various other statistics and/or activities may be displayed in selected other ones of the information boxes 110. As shown in FIG. 3, a menu 130 of selectable items (or tabs) may be provided in order to enable the user to easily select any one of the tabs and access the corresponding module and/or functionality associated with each selectable tab.

Figure 4:
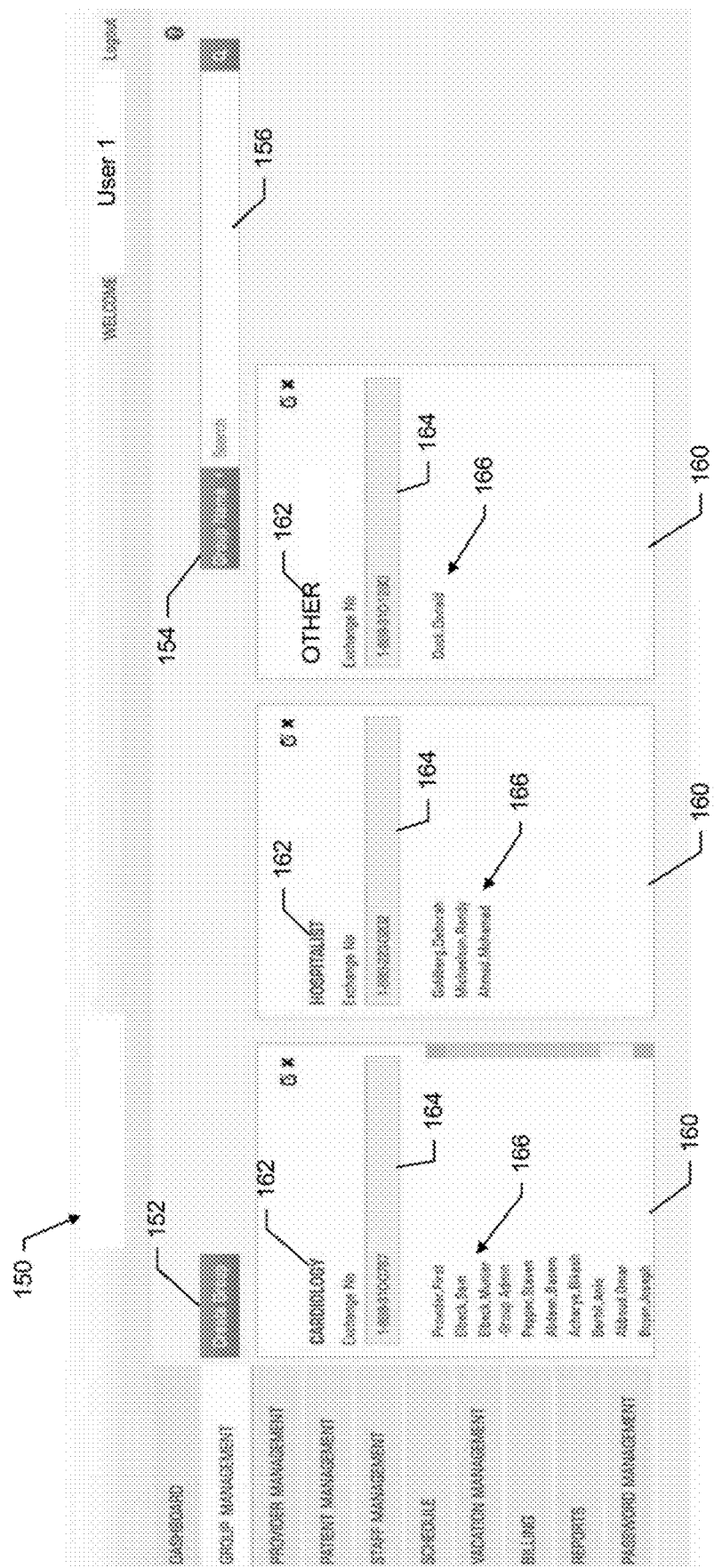
FIG. 4 illustrates an example group management page according to an example embodiment.

FIG. 4 illustrates an interface console 150 associated with the group management function of the group management engine 44. Thus, for example, the user may interface with the group management engine 44 to accomplish group creation, group selection and various other tasks associated with groups and group members via the interface console 150. In particular, a group creation icon 152 is provided to enable the user to define a new group. A group selection icon 154 may be provided to, when selected, present a list of groups that are currently in existence within the system 10. The user may then select a group from a menu or listing of the groups. A search field 156 may also be provided to enable the user to enter search terms to find a particular group by the name of the group of the members of the group.

In some cases, one or more of the existing groups (or a selected group) may be displayed in a group information window 160. The group information window 160 may include a name or identity of the group as a group identifier 162. The group information window 160 may also display an exchange number 164 for the corresponding group, and a group member listing 166. The exchange number 164 is issued for the group immediately when the group is created and is unique for each group. Thus, for example, as soon as the group creation icon 152 is employed to create a group (e.g., by providing the group identifier 162 and populating the group with members to create the group member listing 166), the exchange number 164 is both selected and activated. As such, immediately after the group is created, an active telephone number for interacting with group members through any of the modules of the group management engine 44 is also created and can be called.

The communication module 84 may be configured to manage the activation of the exchange number 164 for a particular group responsive to group creation. The communication module 84 may also provide a structured process flow for handling of calls made to the exchange number 164. For example, the communication module 84 may be configured to define a menu of options that are to be presented to the caller when the exchange number 164 is called. The caller may therefore be guided through options for interacting with either the communication module 84 or other modules to carry out desired functions or interactions.

In some cases, certain interactions that are conducted with the modules of the group management engine 44 may result in actionable information or notifications that should be provided to other parties (e.g., physicians, nurses, patients, management, etc.). In such cases, the communication module 84 may be further configured to execute notification procedures and/or message routing to ensure that the notifications/information is distributed to the correct parties. For example, if a service provider (e.g., a physician) logs into the system 10 via one of the clients 20 (e.g., a smartphone of the service provider), the service provider may access the physician management module 82 to request a schedule adjustment or otherwise provide information on availability that is pertinent to the generation of or modification of the dynamically updateable reference schedule 90. The schedule adjustment request or information on availability may then be routed by the communication module 82 to the proper scheduling authority (e.g., a department or group manager) to have the dynamically updateable reference schedule 90 adjusted or generated accordingly. If others are impacted by the adjustment or need to be informed of generation of the dynamically updateable reference schedule 90, the communication module 82 may further handle notifications to those parties.

Figure 5:
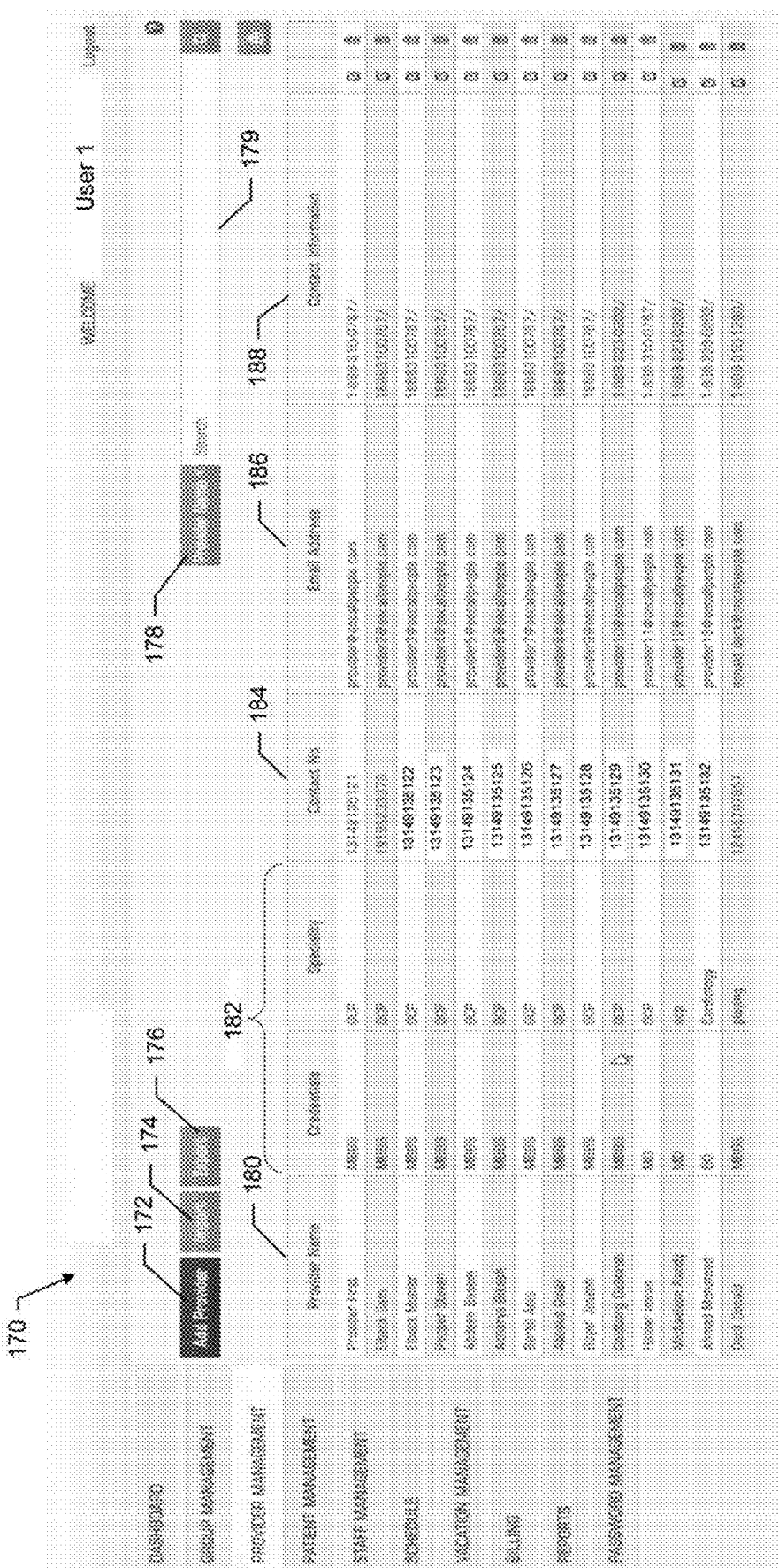
FIG. 5 illustrates an example provider management page according to an example embodiment.

FIG. 5 illustrates an interface console 170 associated with the provider management function of the group management engine 44. Thus, for example, the user may interface with the group management engine 44 to access information about the providers that are available for inclusion in one or more of the groups. Thus, for example, the interface console 150 may be used to add new providers, modify existing providers, or select individual providers from a roster of providers to associate the selected providers with any one (or more) of the groups that have been created.

As shown in FIG. 5, the interface console 170 may include an add provider icon 172 that can be selected in order to enable the user to create a new provider. Alternatively, an entire roster or listing of providers can be imported from an external source (e.g., a spreadsheet or database) via the import icon 174. Similarly, the roster associated with a particular organization or group may be exported to a spreadsheet, database, or other application via an export icon 176. A provider name icon 178 may be selected to obtain an alphabetized or otherwise organized listing of providers. Alternatively, a search field 179 may be provided to enable searching by name (first or last), or by any other identifying information that may be associated with the providers.

A provider name column 180 may be presented in the interface console 170 to list the names of each provider who is listed as a service provider (e.g., a physician) within the system 10. In some cases, one or more columns may also be provided for associating qualifications or other qualifying information 182 associated with each respective one of the providers. The qualifying information 182 may include specialties, credentials, and/or the like. Each of the providers may also have respective contact numbers associated therewith. The contact number column 184 may least each of the respective telephone numbers (landline or cell) that can be used to reach a corresponding one of the providers when the provider is on call. The telephone numbers may, in some cases, be limited to cell numbers so that text messaging can be conducted to the corresponding telephone numbers. In an example embodiment, when a caller calls into the system 10 via one of the exchange numbers 164, the caller may be routed to a series of audio menu prompts that may enable the caller (e.g., via touch pad entry or voice command) to select options that may ultimately include reaching the on-call provider based on consulting the dynamically updateable reference schedule 90 as described above. When the caller selects the option to call the on-call provider, the corresponding number listed in the contact number column 184 for the one of the providers that is currently on-call will be dialed. The caller can thereby be connected to the on-call provider directly.

The interface console 170 may also include an address column 186 for storing an email address or other contact address for each respective one of the providers. The email addresses may provide an avenue by which to reach specific ones or groups of the providers for notification or other informational purposes. For example, if the dynamically updateable reference schedule 90 is modified (or not) in a way that impacts a particular provider, an email may be sent to the particular provider to inform the particular provider of the modification (or that the modification was not approved if the modification was requested by the particular provider). Other notifications and communications may also be conducted between parties or entities associated with the system 10 via the information associated with each of the providers from the address column 186.

Each one of the providers may also be associated with a specific group (or groups) of which the corresponding provider is a member. A group contact number column 188 may also be provided to list the corresponding group-specific contact number (e.g., the exchange number 164 of the corresponding group). Thus, the group-specific contact number for each of the providers is not unique to the provider, but is instead common to all members of the group. As mentioned above, the provider name column 180 is effectively a roster or listing of all available providers from which individual providers can be selected to be added to a group, either when the group is initially created or when to modify the membership of an existing group. Once associated with a particular group, the providers of the particular group can each be reached during their on-call times via the communication module 84 based on referencing the dynamically updateable reference schedule 90 that is generated and maintained by the scheduling module 80. Meanwhile, the roster of physicians or providers and various aspects of group creation/modification and tasking of providers within groups may be handled by the physician management module 82.

Figure 7:
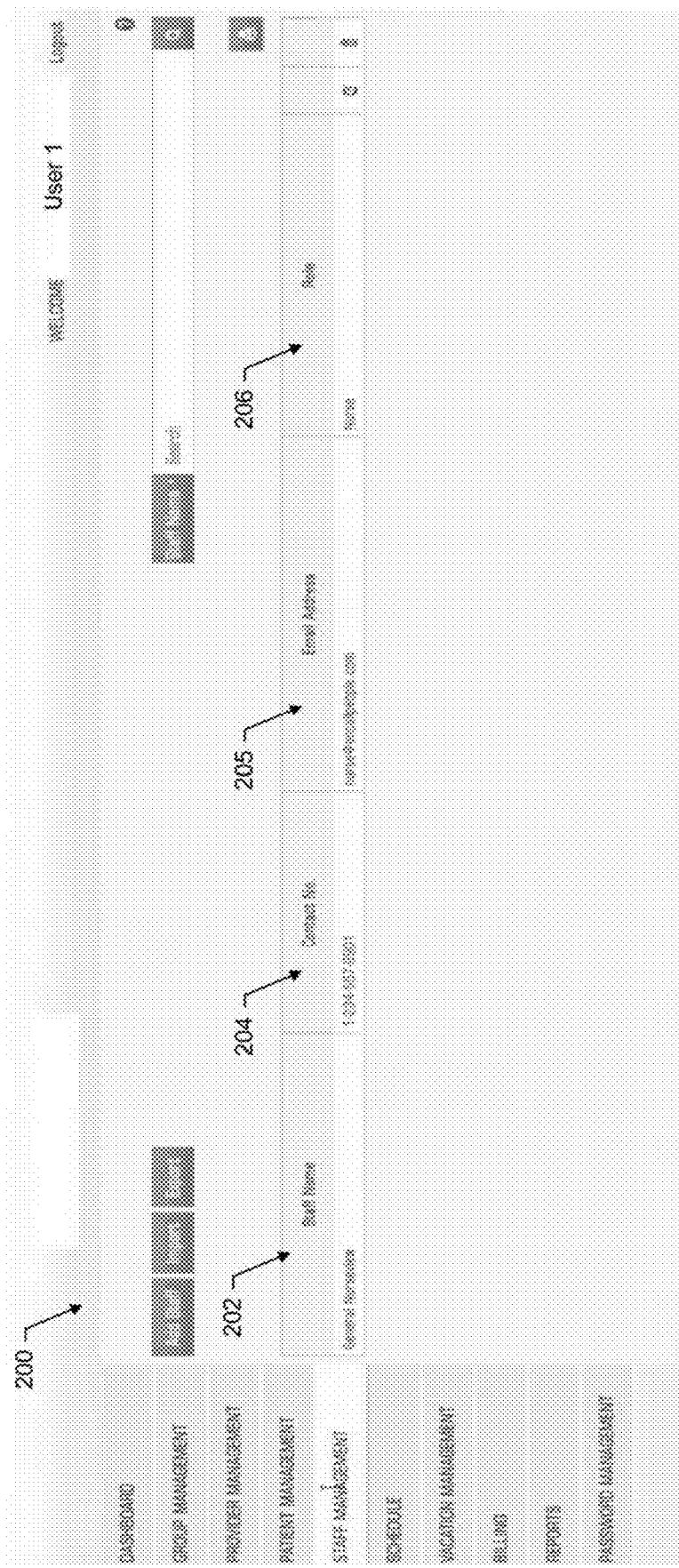
FIG. 7 illustrates an example staff management page according to an example embodiment.
Figure 8:
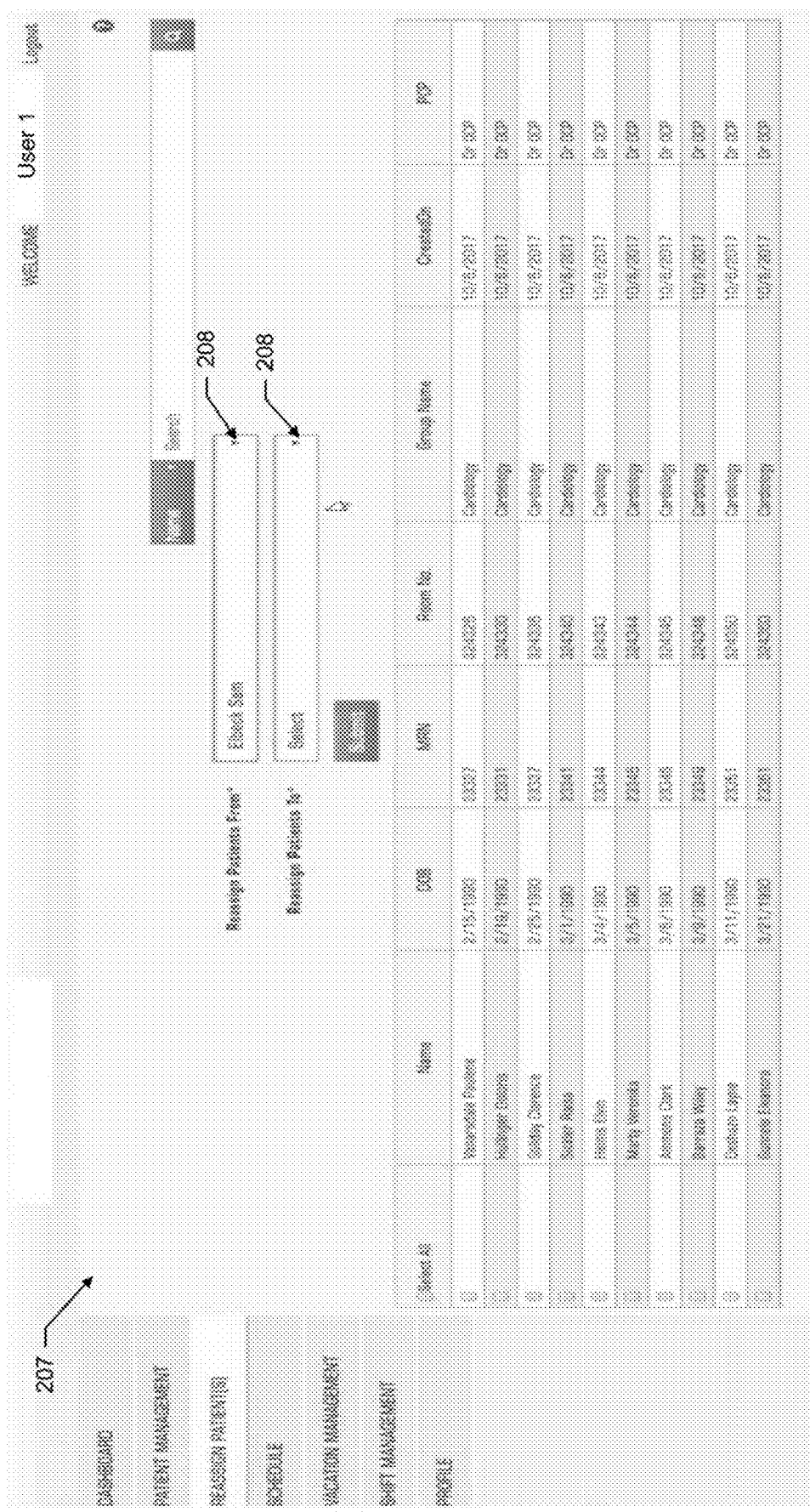
FIG. 8 illustrates a patient reassignment page according to an example embodiment.

In some example embodiments, the group management engine 44 may be configured to provide tools for patient management and staff management as well. In this regard, FIG. 6 illustrates a web page 190 for a patient management tab and FIG. 7 illustrates a web page 200 for a staff management tab generated by the group management engine 44 of an example embodiment. The web page 190 for patient management is structured to include patient information that includes patient identifier information 192 (e.g., name and date of birth), information regarding the attending provider 194, location information and notes 196 regarding care. The web page 200 for staff management is structured to include staff identifier information 202 (e.g., name), contact information including a telephone number 204 and email address 205, and information indicative of the role of the staff member 206. Patients or staff from the listing or roster of patients and staff provided under the patient management tab and the staff management tab, respectively, can be associated with groups, physicians or activities, and can be specifically tied to the dynamically updateable reference schedule 90. The addition of patients/staff members, importation or exportation of patient lists and searching for patients/staff may also be conducted in similar fashion to the corresponding functionalities described above in reference to the roster or listing of physicians and groups.

Figure 9:
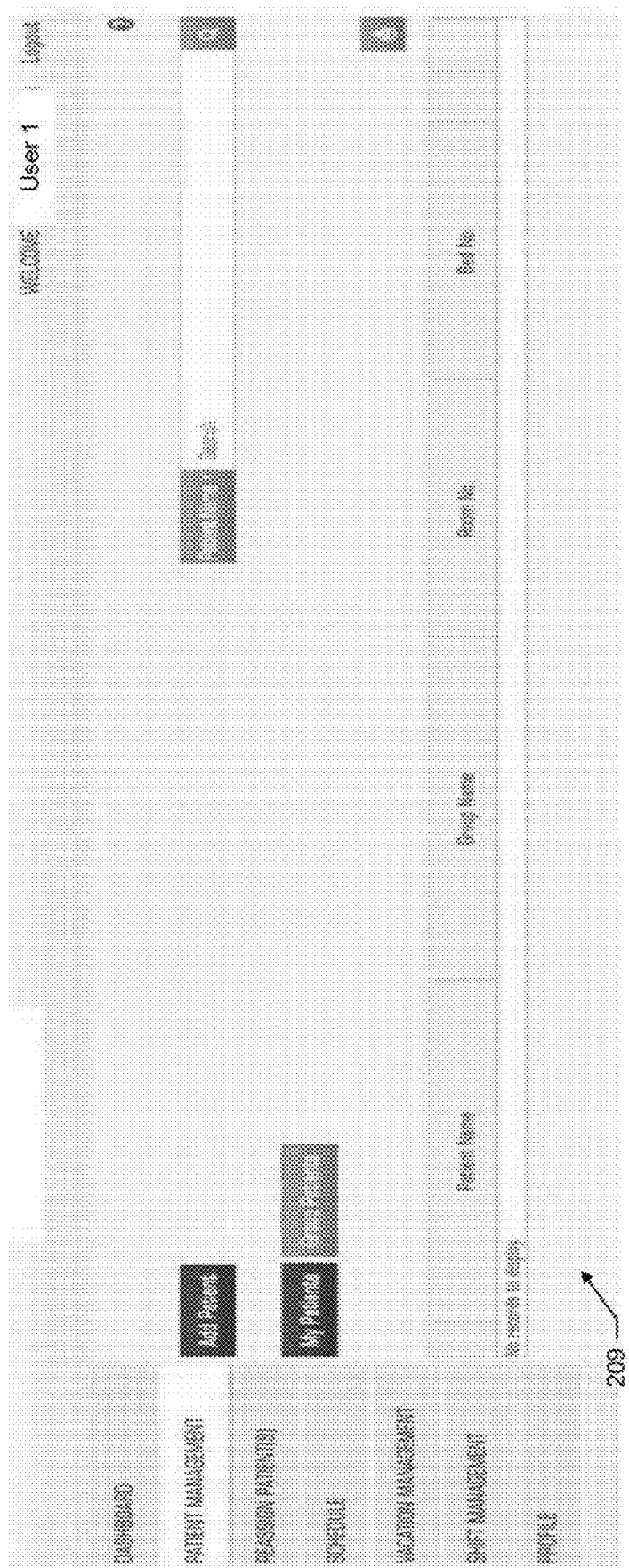
FIG. 9 illustrates an interface for adding patients, searching for patients and assigning patients according to an example embodiment.

Referring again to patient management, it may also be possible to reassign patients between providers. For example, the web page 207 of FIG. 8 may be used to select patients for reassignment between providers that can be designated in corresponding selection windows 208 provided in the web page 207. The reassignment of patients via this mechanism can transfer all patient information (including provider notes) to the newly assigned provider in a completely secure manner (i.e., no one other than the two providers have access to the information being transferred) that is HIPAA compliant. FIG. 9 illustrates a web page 209 associated with generation of new patient information. In this regard, the web page 209 may be used to add new patients, search for patients by name, or group patients by provider or group associations.

Figure 10:
FIG. 10 illustrates a graphical display representative of a portion of a dynamically updateable reference schedule according to an example embodiment.

As shown in FIG. 10, the group management engine 44 may be configured to generate a display 210 representative of a portion of the dynamically updateable reference schedule 90 under a schedule tab. When the schedule tab is selected, a portion of the dynamically updateable reference schedule 90 may be displayed in calendar form displaying a selected or desired period of time (e.g., month, week, day, etc.). The portion displayed is also limited to a single group (i.e., selected group 212). The content displayed (i.e., the providers associated with any shifts or temporally defined calendar segments) may also be provided such that the user can select mechanisms by which to differentiate providers by function or task (e.g., rounding, admitting or on call physicians by shift). Thus, the user can select a temporal display paradigm and a content display paradigm for the display 210. The contents of the display 210 are determined by referencing the dynamically updateable reference schedule 90 to build the display 210 according to the temporal display paradigm and the content display paradigm that has been selected (e.g., by default or by user selection).

In the example of FIG. 10, the providers that are associated with each day are listed and color coded according to their function (e.g., rounding, admitting or on call). For this particular schedule, the provider assigned or listed for shifts that are outside normal working hours is effectively on call during the corresponding shift, and the display 210 indicates (via on call icon 212) that the corresponding provider is the on call provider for that temporal segment. For temporal segments (or shifts) where multiple providers are active, only one of the providers may be indicated as being on call (via the on call icon 212). Calls that come into the exchange number 164 during a particular temporal segment will be automatically routed to the provider associated with the on call icon 212. However, a user referencing the display 210 can also call the corresponding provider by selecting the on call icon 212.

As shown in FIG. 10, tools 220 may be provided in connection with the display 210 to enable the user (assuming proper credentials or permissions apply) to create new schedules, insert providers into open shifts, replace providers assigned to a given shift, replace providers with open shifts, or replace an on call provider with another provider. Any changes made using the tools 220 are immediately made to the dynamically updateable reference schedule 90 and therefore propagate through the system to provide notifications (via the communication module 82) and update the display 210 so that the all functions and aspects of the dynamically updateable reference schedule 90 are modified in real time.

In a typical environment, managers may be asked to generate a schedule to provide coverage of all necessary temporal segments or shifts for a given period of time. Managers may also separately be asked to manage availability restriction requests (e.g., time off requests, shift change requests or vacation requests) that may come in via email or a separate system. When availability is approved for a particular provider, if the manager mistakenly assigns the provider to cover a shift during the period that the provider will be on vacation, the manager may be required to adjust the schedule when the error is discovered, and the adjustment may impact several other providers. During holidays or periods where availability of providers is scarce, this can create very difficult situations to overcome. The group management engine 44 may integrate not only all of the automatic issuance of notifications and communications needed to ensure that everyone is aware of schedules and schedule changes, but also the generation and modification of the schedule itself. In this regard, since the dynamically updateable reference schedule 90 is available or connected to every module and function, it is possible to avoid schedule conflicts since the manager will not be allowed to make mistakes by the group management engine 44.

Figure 12:
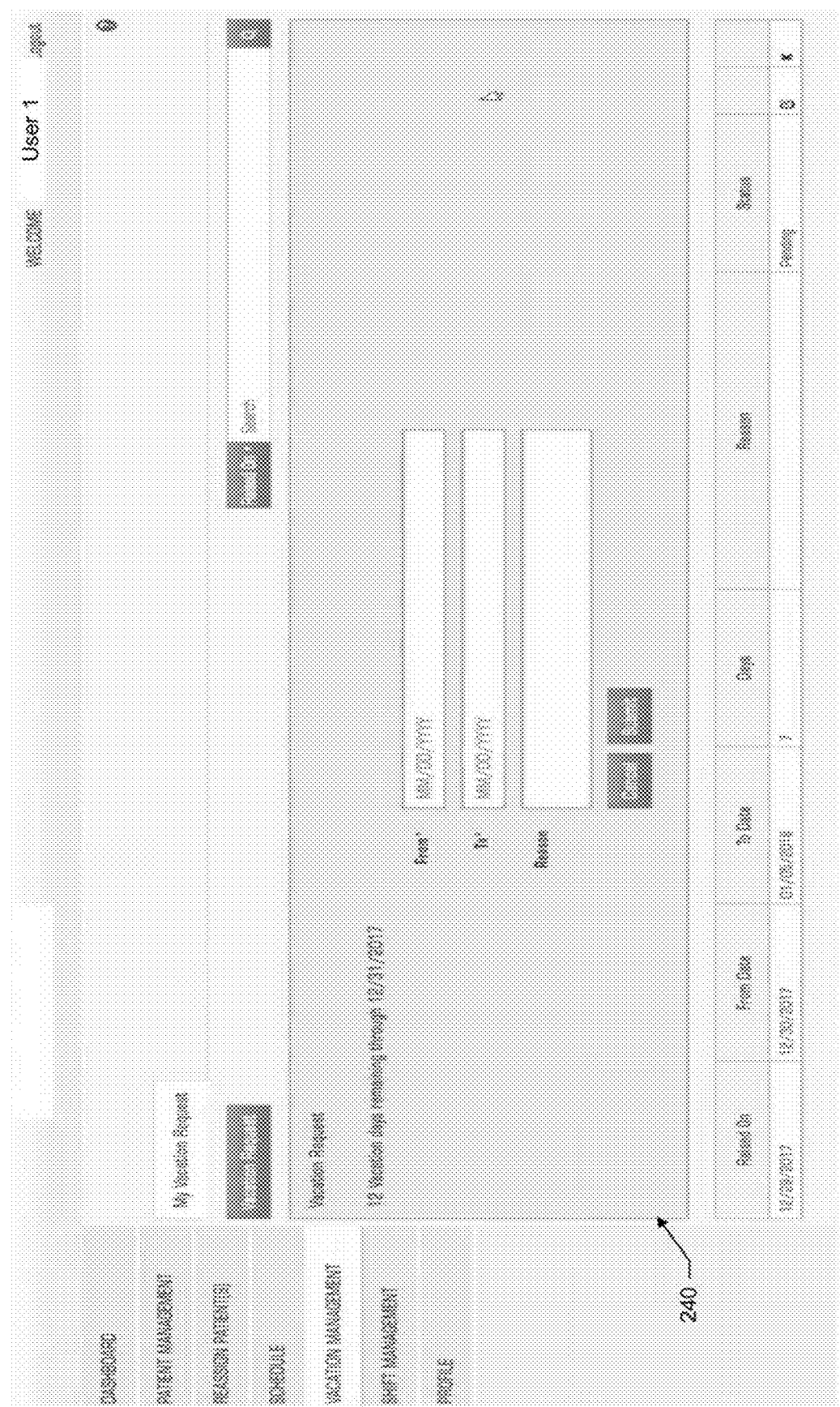
FIG. 12 illustrates an example vacation (or time off) request page according to an example embodiment.
Figure 13:
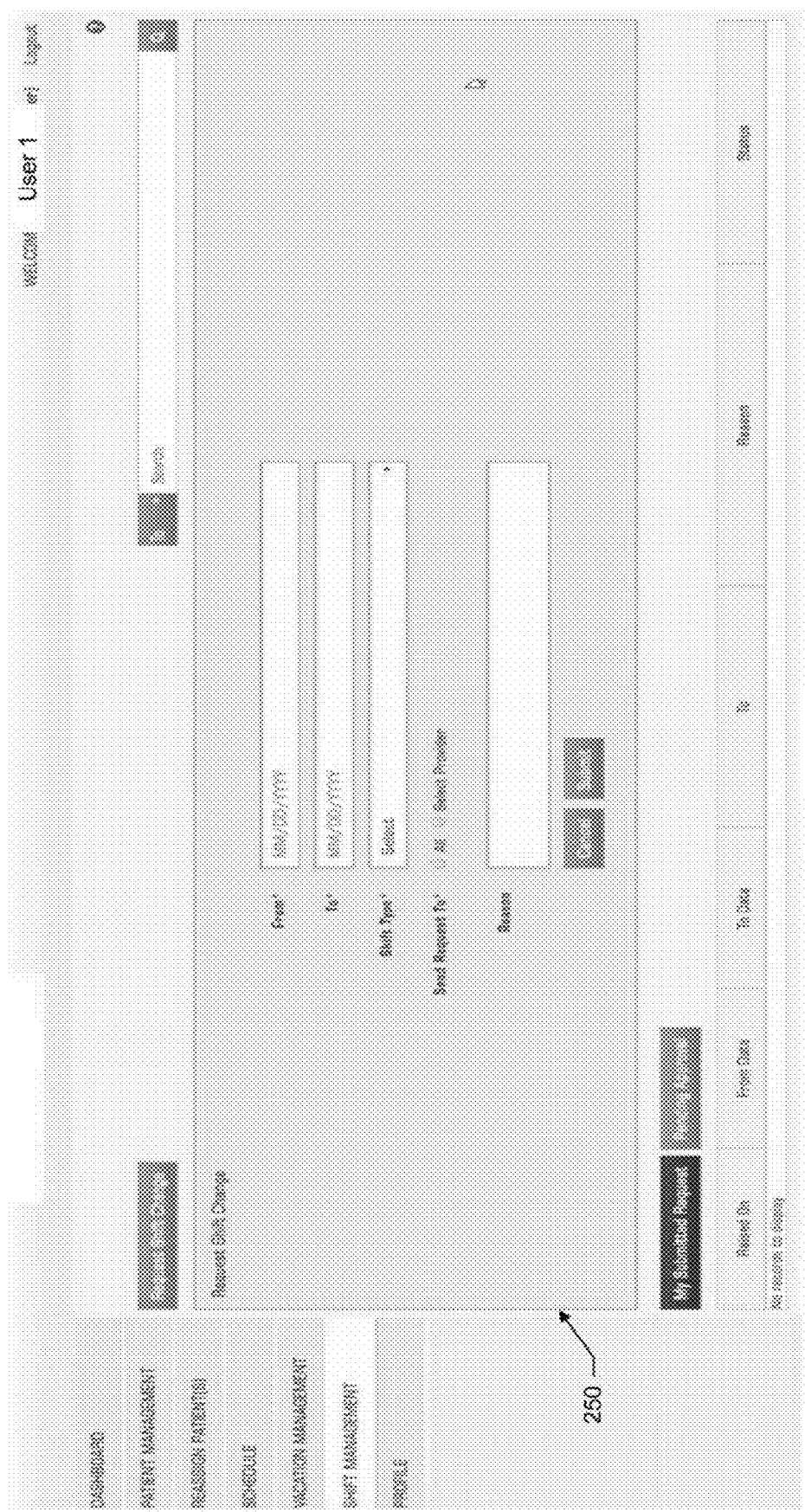
FIG. 13 illustrates an example shift management page according to an example embodiment.

As such, in some embodiments, the group management engine 44 may be configured to enable individual providers and managers to submit and manage requests for vacation (or other time off) and shift changes via the system 10 as well. As such, for example, a vacation management tab may be provided which, when selected, generates a web page 230 (see FIG. 11) that displays a summary of vacation (or time off) requests by provider, group, manager, or the like. In this regard, each entry 232 in a listing of requests 234 may indicate the date range, provider, reasons, and/or date of application. Meanwhile, FIG. 12 illustrates a web page 240 for a provider to provide details for requesting time off or vacation time, and FIG. 13 illustrates a web page 250 that enables a provider to provide details for requesting a shift change.

Figure 11:
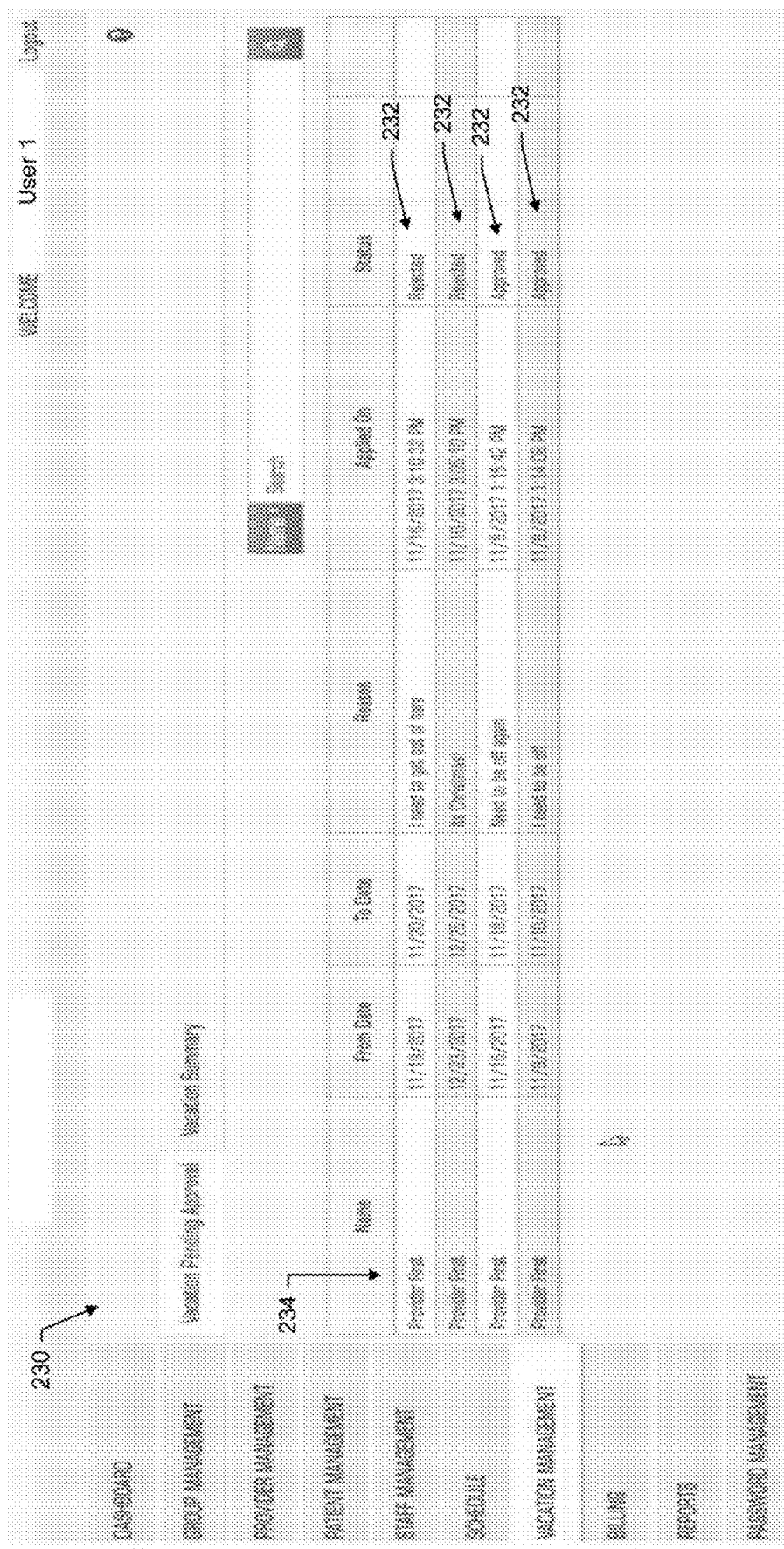
FIG. 11 illustrates an example vacation management page according to an example embodiment.

As shown in FIG. 11, a status of each entry 232 may be indicated to show whether a decision has been made and if the decision is either to approve or reject the corresponding entry 232. The user (if the user is a manager) may make a determination regarding each entry 232 and update the status in the vacation management tab. When the status is updated, the update may be made to the dynamically updateable reference schedule 90 so that corresponding changes can be propagated throughout the system. For example, if a provider has a request approved, the dynamically updateable reference schedule 90 may block entry of the provider into any shift or temporal segment that is within the date range of the corresponding entry. Accordingly, the requests/approvals of vacations or other availability restriction requests are automatically tied to the scheduling/assignment functions so that the manager need not separately keep track of who is available or unavailable and when. Instead, the dynamically updateable reference schedule 90 integrates all aspects of management, scheduling and communication in one location to avoid conflicts and simplify/automate the provision of information to the parties impacted by any decisions.

Figure 14:
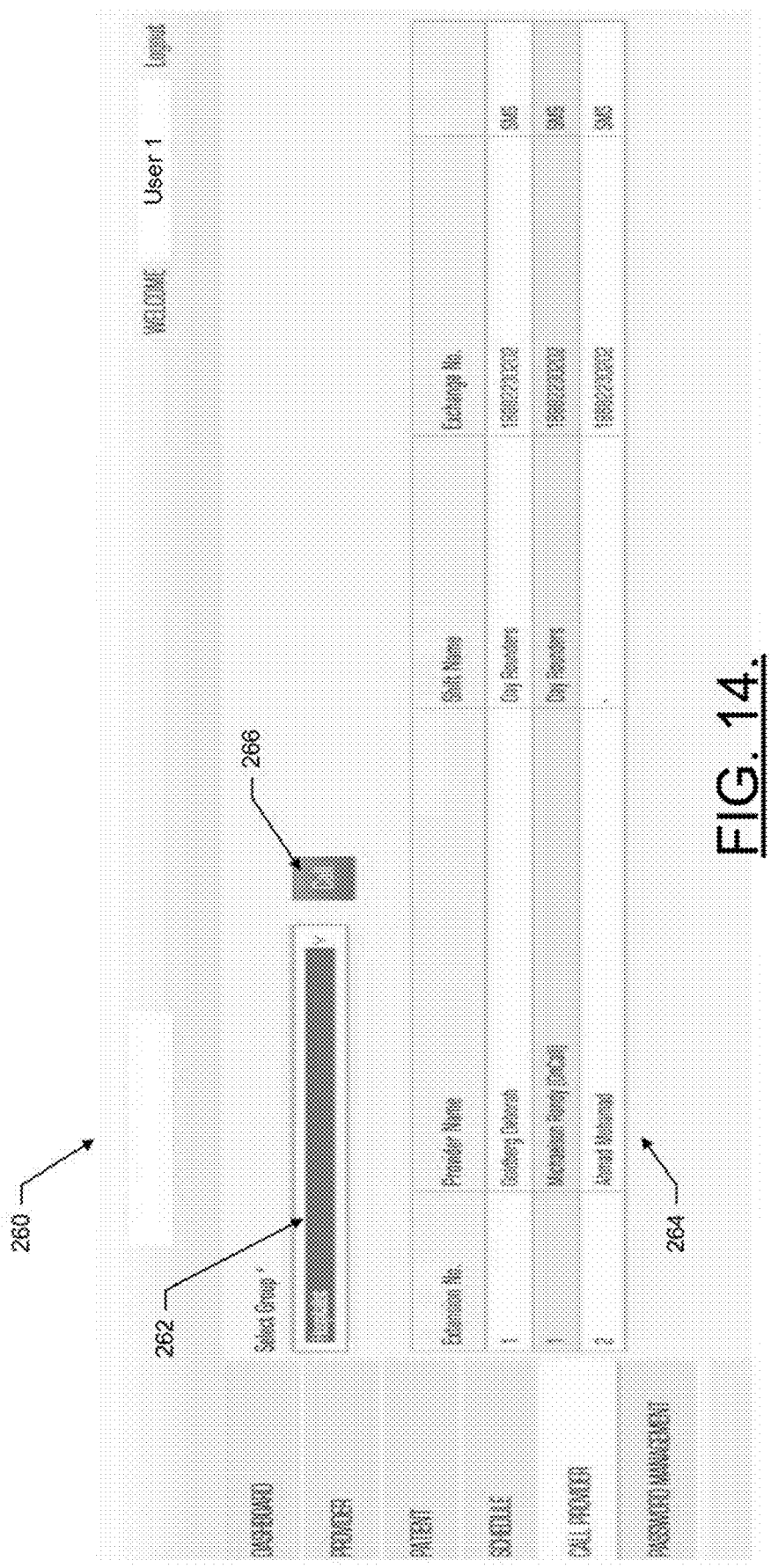
FIG. 14 illustrates a call provider contact page according to an example embodiment.

Referring now to FIG. 14, a web page 260 is illustrated for defining call providers for a particular group. In this regard, a group selector 262 is provided to enable the user to select any one of the groups that the user has access to manage or otherwise interface with. A call roster 264 may then be displayed indicating the exchange number 164 for the group, a shift name for the temporal segment to which assignments are being made, along with the provider's names and extensions. The web page 260 may be presented to a user (e.g., a nurse) who is looking for an identity of the on call provider independent of the schedule (of FIG. 10). However, the user may be enabled to call the on call provider directly from the web page 260 by simply selecting the call icon 266, which is provided on the web page 260. Accordingly, the user need not make a separate call, but can instead initiate a call to the exchange number 164 for the group directly though the interface provided.

From a technical perspective, the group management engine 44 described above may be used to support some or all of the operations described above. As such, the platform described in FIG. 2 may be used to facilitate the implementation of several computer program and/or network communication based interactions within the system 10 shown in FIG. 1. As an example, FIGS. 15 and 16 each represent a flowchart of a method and program product according to an example embodiment of the invention. It will be understood that each block of the flowcharts, and combinations of blocks in the flowcharts, may be implemented by various means, such as hardware, firmware, processor, circuitry and/or other device associated with execution of software including one or more computer program instructions. For example, one or more of the procedures described above may be embodied by computer program instructions. In this regard, the computer program instructions which embody the procedures described above may be stored by a memory device of a user terminal (e.g., client 20, application server 40, and/or the like) and executed by a processor in the user terminal. As will be appreciated, any such computer program instructions may be loaded onto a computer or other programmable apparatus (e.g., hardware) to produce a machine, such that the instructions which execute on the computer or other programmable apparatus create means for implementing the functions specified in the flowchart block(s). These computer program instructions may also be stored in a computer-readable memory that may direct a computer or other programmable apparatus to function in a particular manner, such that the instructions stored in the computer-readable memory produce an article of manufacture which implements the functions specified in the flowchart block(s). The computer program instructions may also be loaded onto a computer or other programmable apparatus to cause a series of operations to be performed on the computer or other programmable apparatus to produce a computer-implemented process such that the instructions which execute on the computer or other programmable apparatus implement the functions specified in the flowchart block(s).

Accordingly, blocks of the flowcharts support combinations of means for performing the specified functions and combinations of operations for performing the specified functions. It will also be understood that one or more blocks of the flowcharts, and combinations of blocks in the flowcharts, can be implemented by special purpose hardware-based computer systems which perform the specified functions, or combinations of special purpose hardware and computer instructions.

Figure 15:
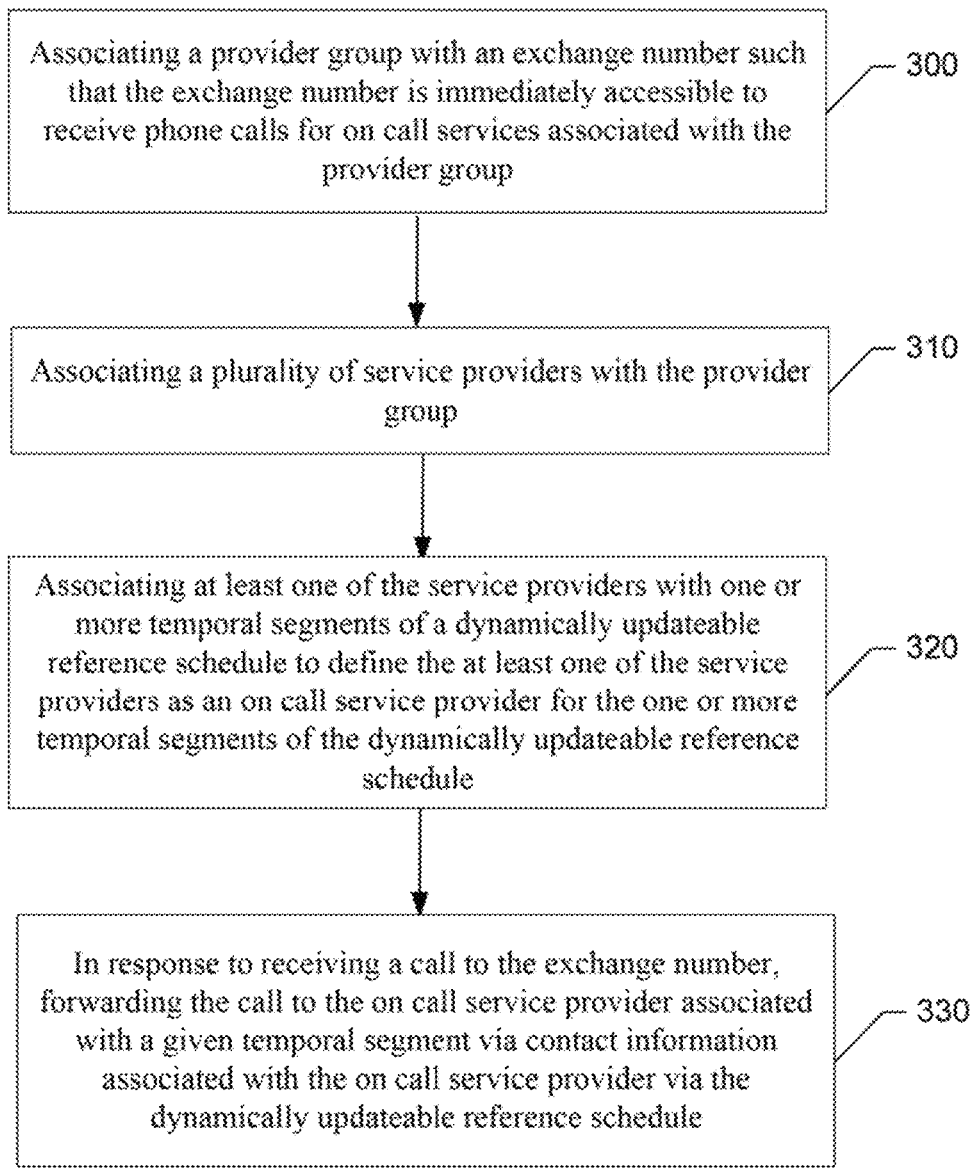
FIG. 15 illustrates a block diagram of a method for providing electronic group management that integrates scheduling, personnel management and communication functions in accordance with an example embodiment.

In this regard, a method according to one embodiment of the invention is shown in FIG. 15. The method may provide electronic group management that integrates scheduling, personnel management and communication functions. The may include associating a provider group with an exchange number such that the exchange number is immediately accessible to receive phone calls for on call services associated with the provider group at operation 300. The method may further include associating a plurality of service providers with the provider group at operation 310 and associating at least one of the service providers with one or more temporal segments of a dynamically updateable reference schedule to define the at least one of the service providers as an on call service provider for the one or more temporal segments of the dynamically updateable reference schedule at operation 320. The method may also include, in response to receiving a call to the exchange number, forwarding the call to the on call service provider associated with a given temporal segment via contact information associated with the on call service provider via the dynamically updateable reference schedule at operation 330.

In some embodiments, the method of FIG. 15 (and corresponding apparatus configured to perform the method) may include (or be configured to perform) additional, optional operations, and/or the operations described above may be modified or augmented. Some examples of modifications, optional operations and augmentations are described below. It should be appreciated that the modifications, optional operations and augmentations may each be added alone, or they may be added cumulatively in any desirable combination. For example, in some cases, the method may further include associating a plurality of provider groups with a corresponding plurality of exchange numbers, where each of the exchange numbers is automatically and immediately available to receive a call responsive to creation of a corresponding one of the provider groups, and the method may further include associating the plurality of service providers with respective ones of the plurality of provider groups. In an example embodiment, the method may further include generating a display representative of a portion of the dynamically updateable reference schedule, the portion of the dynamically updateable reference schedule being displayed in calendar form corresponding to a user selected period of time. In some cases, the one or more temporal segments may be associated with a corresponding on call provider for each of the one or more temporal segments on the display. In an example embodiment, the method may further include generating an icon on the display to enable initiation of the call to a current on call provider by selection of the icon on the display. In some cases, the service providers may be physicians.

Thus, for example, some embodiments may provide an electronic group management SaaS based solution that creates efficiency in managing medical groups with the goal of improving care for patients and quality of life for physicians. Example embodiments may therefore utilize several variable inputs to produce a 'dynamic call-in enabled schedule' that can be simply managed and updated by either a group manager or by the providers themselves. The integration of a call-in number with the dynamic schedule allows for accurate routing of communication to the correct provider at any given time without any intervention. Furthermore, the ability for each provider to update their availability in real time, request vacation days, hand off patient responsibilities to other providers, easily dictate notes, and manage their own schedule creates a very highly efficient and communicative group that facilitates accurate and precise communication and improved medical care for patients using a single and dynamic technical link (i.e., the dynamically updateable reference schedule) for integration of scheduling, personnel management and communication functions.

Figure 16:
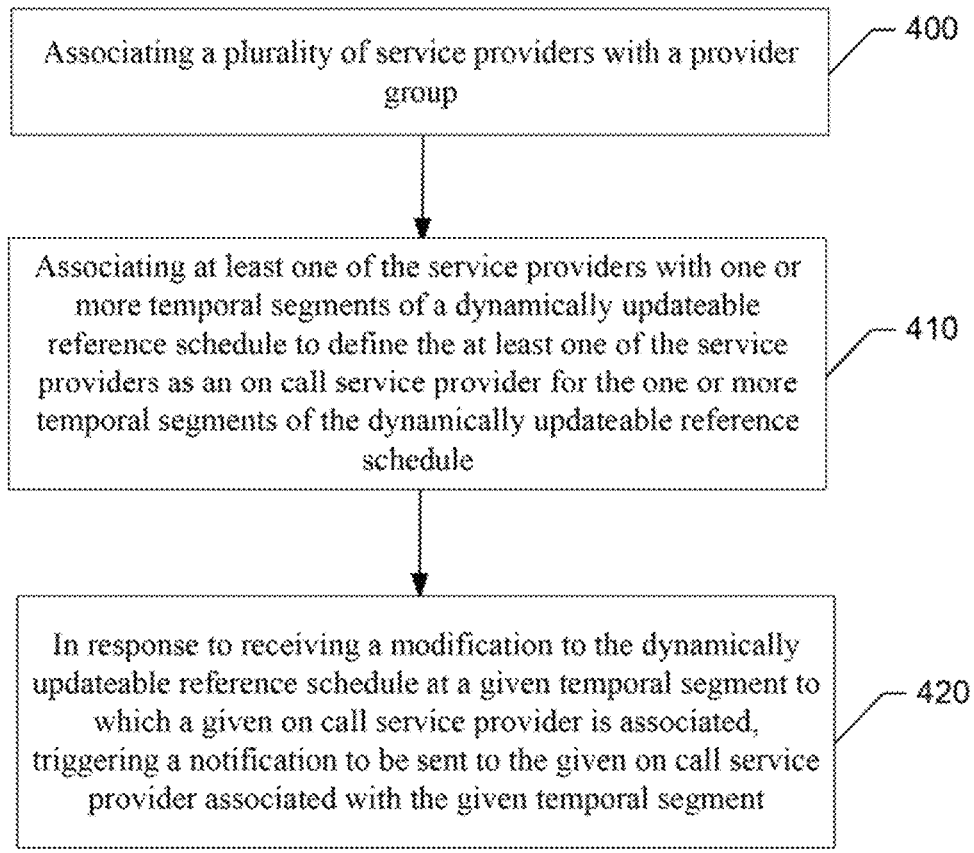
FIG. 16 illustrates a block diagram of another method for providing electronic group management that integrates scheduling, personnel management and communication functions in accordance with an example embodiment.

The method of FIG. 15 effectively creates an on call group that can be reached immediately via the dynamically updateable reference schedule. However, as mentioned above, notifications of certain activities can also be performed in example embodiments. FIG. 16 illustrates a method of providing electronic group management that integrates scheduling, personnel management and communication functions that addressed the automated information distribution aspect of some embodiments. In this regard, the method may include associating a plurality of service providers with a provider group at operation 400 and associating at least one of the service providers with one or more temporal segments of a dynamically updateable reference schedule to define the at least one of the service providers as an on call service provider for the one or more temporal segments of the dynamically updateable reference schedule at operation 410. The method may further include, in response to receiving a modification to the dynamically updateable reference schedule at a given temporal segment to which a given on call service provider is associated, triggering a notification to be sent to the given on call service provider associated with the given temporal segment at operation 420.

In some embodiments, the method of FIG. 16 (and corresponding apparatus configured to perform the method) may include (or be configured to perform) additional, optional operations, and/or the operations described above may be modified or augmented. Some examples of modifications, optional operations and augmentations are described below. It should be appreciated that the modifications, optional operations and augmentations may each be added alone, or they may be added cumulatively in any desirable combination. For example, in some cases, the method may further include providing an interface to enable secure patient transfer between service providers. In an example embodiment, the method may further include receiving an indication of a request and a corresponding time range of unavailability for an unavailable service provider, enabling a user to grant the request, and, in response to the request being granted, triggering the notification to the unavailable service provider and removing the unavailable service provider from or preventing the unavailable service provider from association with temporal segments that overlap the corresponding time range of unavailability. In some cases, the method may further include triggering a second notification to be sent to at least one other service provider replaced by or replacing the given on call service provider in the dynamically updateable reference schedule at the given temporal segment.

In an example embodiment, an apparatus for performing the method of FIGS. 15 and/or 16 above may comprise a processor (e.g., the processor 52) or processing circuitry configured to perform some or each of the operations (300-330 and/or 400-420) described above. The processor may, for example, be configured to perform the operations (300-330 and/or 400-420) by performing hardware implemented logical functions, executing stored instructions, or executing algorithms for performing each of the operations. In some embodiments, the processor or processing circuitry may be further configured for additional operations or optional modifications similar to those described above in reference to operations 300-330 and/or 400-420. Thus, for example, an apparatus comprising configurable processing circuitry may be configured to perform either the method of FIG. 15, the method of FIG. 16, or a combination of the methods of FIGS. 15 and 16 with or without the modifications described above.

Figure 17A:
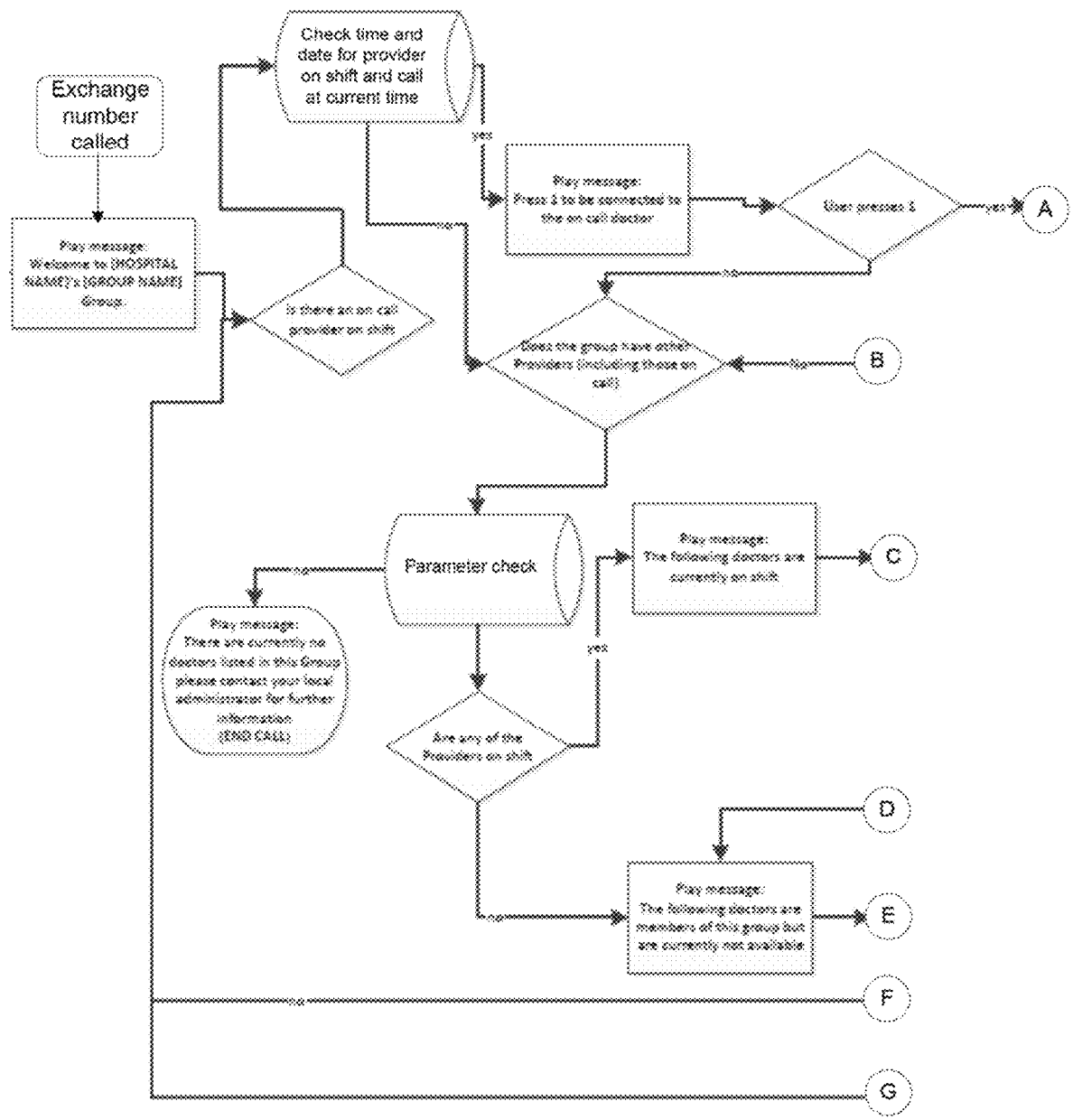
FIGS. 17A and 17B, illustrates a flow diagram for handling of a call for routing to an on call service provider in accordance with an example embodiment.
Figure 17B:
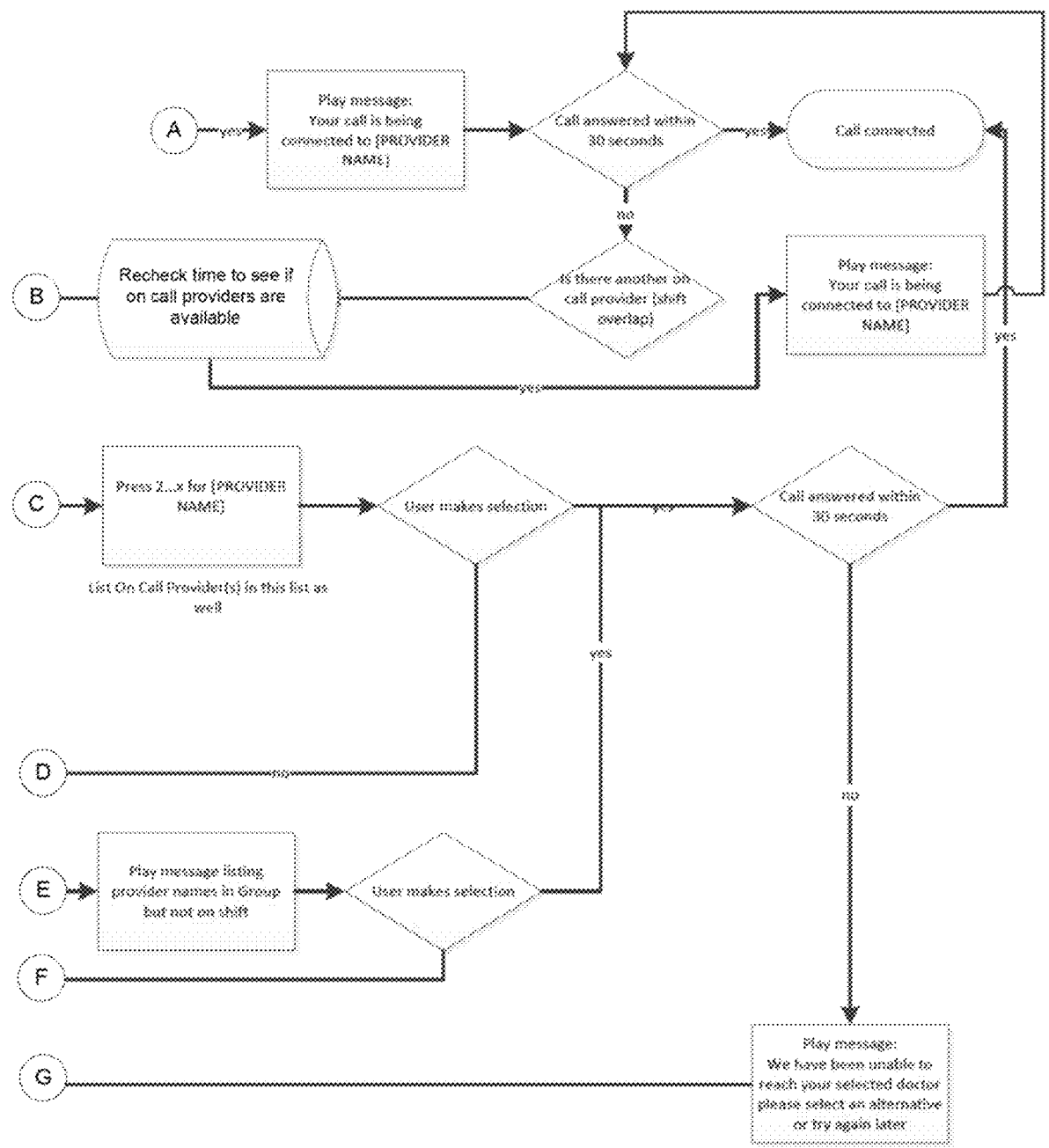

As discussed above, the communication module 84 may define an automated interface enabling voice or key commands to be used to navigate the automated interface. FIG. 17, which is defined by FIGS. 17A and 17B, illustrates a flow diagram for automated handling of a call for routing to an on call service provider in accordance with an example embodiment. In FIG. 17, rectangular blocks are messages played to the user, and cylindrical blocks are checks made to the dynamically updateable reference schedule, triangles are decision blocks or user selections, and rounded rectangles or ovals are actions taken or received.

Many modifications and other embodiments of the inventions set forth herein will come to mind to one skilled in the art to which these inventions pertain having the benefit of the teachings presented in the foregoing descriptions and the associated drawings. Therefore, it is to be understood that the inventions are not to be limited to the specific embodiments disclosed and that modifications and other embodiments are intended to be included within the scope of the appended claims. Moreover, although the foregoing descriptions and the associated drawings describe exemplary embodiments in the context of certain exemplary combinations of elements and/or functions, it should be appreciated that different combinations of elements and/or functions may be provided by alternative embodiments without departing from the scope of the appended claims. In this That which is claimed:

1. A system for providing electronic group management that integrates scheduling, personnel management and communication functions, the system comprising processing circuitry configured to:
associate a provider group with an exchange number, the exchange number being immediately accessible to receive phone calls for on call services associated with the provider group;
associate a plurality of service providers with the provider group; and
associate two or more of the service providers with two or more temporal segments of a dynamically updateable reference schedule to define the two or more of the service providers as an on call service provider for the two or more temporal segments of the dynamically updateable reference schedule,
wherein the dynamically updateable reference schedule provides corresponding voice call contact information and data messaging contact information for each of the service providers of the provider group such that:
calls to the exchange number during a temporal segment from among the two or more temporal segments are forwarded to the on call service provider associated with the temporal segment via voice call contact information of the on call provider, and
a modification to the dynamically updateable reference schedule at the temporal segment triggers a notification to be sent to data messaging contact information of each service provider associated with the temporal segment responsive to a modification to the dynamically updateable reference schedule at the temporal segment.

2. The system of claim 1, wherein the processing circuitry is further configured to instantaneously send the notification responsive to the modification of the dynamically updateable reference schedule.

3. The system of claim 2, wherein each provider associated with the temporal segment includes an original provider assigned to the temporal segment and a replacement provider substituted for the original provider in the dynamically updateable reference schedule.

4. The system of claim 1, wherein the processing circuitry is further configured to receive an indication of a request and a corresponding time range of unavailability for an unavailable service provider,
wherein the processing circuitry is further configured to enable a user to grant the request, and
wherein, in response to the request being granted, the notification is triggered to the unavailable service provider and the unavailable service provider is removed from or prevented from association with temporal segments that overlap the corresponding time range of unavailability.

5. The system of claim 1, wherein the processing circuitry is further configured to generate a display representative of a portion of the dynamically updateable reference schedule, the portion of the dynamically updateable reference schedule being displayed in calendar form corresponding to a user selected period of time.

6. The system of claim 5, wherein the two or more temporal segments are associated with a corresponding on call provider for each of the two or more temporal segments on the display.

7. The system of claim 6, wherein the display provides an icon to enable initiation of a call to a current on call provider by selection of the icon on the display.

8. The system of claim 1, wherein the processing circuitry is configured to generate a listing of on call providers associated with the provider group for a selected temporal segment, and wherein an icon is provided to enable initiation of a call to a current on call provider through the system.

9. The system of claim 1, wherein the processing circuitry is configured to associate a plurality of provider groups with a corresponding plurality of exchange numbers, each of the exchange numbers being automatically and immediately available to receive a call responsive to creation of a corresponding one of the provider groups.

10. The system of claim 1, wherein the service providers are physicians.

11. A method for providing electronic group management that integrates scheduling, personnel management and communication functions, the method comprising:
associating a provider group with an exchange number, the exchange number being immediately accessible to receive phone calls for on call services associated with the provider group;
associating a plurality of service providers with the provider group;
associating two or more of the service providers with two or more temporal segments of a dynamically updateable reference schedule to define the two or more of the service providers as an on call service provider for the two or more temporal segments of the dynamically updateable reference schedule; and
in response to receiving a call to the exchange number during a temporal segment from among the two or more temporal segments, forwarding the call to the on call service provider associated with the temporal segment via contact information associated with the on call service provider via the dynamically updateable reference schedule.

12. The method of claim 11, further comprising associating a plurality of provider groups with a corresponding plurality of exchange numbers, each of the exchange numbers being automatically and immediately available to receive a call responsive to creation of a corresponding one of the provider groups, and associating the plurality of service providers with respective ones of the plurality of provider groups.

13. The method of claim 11, further comprising generating a display representative of a portion of the dynamically updateable reference schedule, the portion of the dynamically updateable reference schedule being displayed in calendar form corresponding to a user selected period of time.

14. The method of claim 13, wherein the two or more temporal segments are associated with a corresponding on call provider for each of the two or more temporal segments on the display.

15. The method of claim 14, further comprising generating an icon on the display to enable initiation of the call to a current on call provider by selection of the icon on the display.

16. The method of claim 11, wherein the service providers are physicians.

17. A method for providing electronic group management that integrates scheduling, personnel management and communication functions, the method comprising:

associating a plurality of service providers with a provider group;

associating two or more of the service providers with two or more temporal segments of a dynamically updateable reference schedule to define the two or more of the service providers as an on call service provider for the two or more temporal segments of the dynamically updateable reference schedule; and in response to receiving a modification to the dynamically updateable reference schedule at a modified temporal segment from among the two or more temporal segments to which a selected on call service provider is associated, triggering a notification to be sent to the selected on call service provider associated with the modified temporal segment.

18. The method of claim 17, further comprising providing an interface to enable secure patient transfer between service providers.

19. The method of claim 17, further comprising receiving an indication of a request and a corresponding time range of unavailability for an unavailable service provider, enabling a user to grant the request, and in response to the request being granted, triggering the notification to the unavailable service provider and removing the unavailable service provider from or preventing the unavailable service provider from association with temporal segments that overlap the corresponding time range of unavailability.

20. The method of claim 17, further comprising triggering a second notification to be sent to at least one other service provider replaced by or replacing the selected on call service provider in the dynamically updateable reference schedule at the modified temporal segment.

\* \* \* \* \*